US012391997B2

(12) United States Patent
Lee et al.

(10) Patent No.: US 12,391,997 B2
(45) Date of Patent: Aug. 19, 2025

(54) **METHOD FOR DETERMINING THE PRESENCE OR ABSENCE OF *M. TUBERCULOSIS*, *M. BOVIS* AND *M. BOVIS* BCG IN A SAMPLE**

(71) Applicant: SEEGENE, INC., Seoul (KR)

(72) Inventors: Kwang-Il Lee, Seoul (KR); Mi Seon Lee, Gyeonggi-do (KR)

(73) Assignee: SEEGENE, INC., Seoul (KR)

( * ) Notice: Subject to any disclaimer, the term of this patent is extended or adjusted under 35 U.S.C. 154(b) by 1308 days.

(21) Appl. No.: 16/959,453

(22) PCT Filed: Dec. 28, 2018

(86) PCT No.: PCT/KR2018/016910
§ 371 (c)(1),
(2) Date: Feb. 25, 2021

(87) PCT Pub. No.: WO2019/135567
PCT Pub. Date: Jul. 11, 2019

(65) Prior Publication Data
US 2022/0090170 A1   Mar. 24, 2022

(30) Foreign Application Priority Data

Jan. 5, 2018   (KR) .......................... 10-2018-0001969

(51) Int. Cl.
*C12Q 1/689* (2018.01)
(52) U.S. Cl.
CPC ......... *C12Q 1/689* (2013.01); *C12Q 2600/16* (2013.01)
(58) Field of Classification Search
CPC .................................. C12Q 1/68; C07H 21/00
See application file for complete search history.

(56) References Cited

U.S. PATENT DOCUMENTS

| 8,357,493 | B2 | 1/2013 | Cole et al. | |
|---|---|---|---|---|
| 2001/0053519 | A1* | 12/2001 | Fodor .................. | G03F 7/265 536/24.1 |
| 2005/0250120 | A1 | 11/2005 | Cole et al. | |

FOREIGN PATENT DOCUMENTS

WO   WO-2004-067702 A2   8/2004

OTHER PUBLICATIONS

Barletta et al., Standardization of a TaqMan-based real-time PCR for the detection of *Mycobacterium tuberculosis*-complex in human sputum American J of Tropical Medicine and Hygiene 91(4) :709 (Year: 2014).*

Halse et al., Evaluation of a single-tube multiplex real-time PCR for differentiation of members of the *Mycobacterium tuberculosis* complex in clinical specimens. Journal of Clinical Microbiology 49(7) :2562 (Year: 2011).*

O'Reilly LM, et al., "The epidemiology of *Mycobacterium bovis* infections in animals and man: a review.", *Tuber Lung Dis*, 1995, 76(Suppl 1):S1-S46.

Brosch R, et al., "A new evolutionary scenario for the *Mycobacterium tuberculosis* complex.", *Proc Natl Acad Sci USA*, 2002, 99(6):3684-3689.

H Li, J C Ulstrup, et al., "Evidence for Absence of the MPB64 Gene in Some Substrains of *Mycobacterium bovis* BCG.", *Infection and Immunity*, 1993, 61(5):1730-1734.

Konno K, et al., "Pyrazinamide Susceptibility and Amidase Activity of Tubercle Bacillj, 1, 2.", *AM ReV Resir Dis*, 1967, 95:461-469.

Morlock GP, et al., "Phenotypic Characterization of pncA Mutants of *Mycobacterium tuberculosis.*", *Antimicrob Agents Chemother*, 2000, 44(9):2291-2295.

Scorpio A, et al., "Mutations in pncA, a gene encoding pyrazinamidase/ nicotinamidase, cause resistance to the antituberculous drug pyrazinamide in tubercle bacillus.", *Nat Med*, 1996, 2(6):662-667.

Garnier T, et al., "The complete genome sequence of *Mycobacterium bovis.*", *Proc Natl Acad Sci USA*, 2003, 100(13):7877-7882.

De la Rua-Domenech R., "Human *Mycobacterium bovis* infection in the United Kingdom: Incidence, risks, control measures and review of the zoonotic aspects of bovine tuberculosis.", *Tuberculosis* (Edinb) 2006, 86:77-109.

Zumarrage MJ, et al., "A 12.7 kb fragment of the *Mycobacterium tuberculosis* genome is not present in *Mycobacterium bovis.*", *Microbiology*, 1999, 145:893-897.

Bakshi CS, et al., "Rapid differentiation of *Mycobacterium bovis* and *Mycobacterium tuberculosis* based on a 12.7-kb fragment by a single tube multiplex-PCR." *Vet Microbiol*, 2005, 109:211-216.

Li, H., et al. (1993) "Evidence for absence of the MPB64 gene in some substrains of *Mycobacterium bovis* BCG.", *Infect. Immun.*, 61(5):1730-1734 (May 1993).

Pinsky, B. A., et al. (2008) "Multiplex Real-Time PCR Assay for Rapid Identification of *Mycobacterium tuberculosis* Complex Members to the Species Level.", *J. Clin. Microbial.*, 46(7):2241-2246 (Jul. 2008).

Singh, S., et al. (2015) "Evolution of *M. bovis* BCG Vaccine: Is Niacin Production Still a Valid Biomarker?", *Tuberculosis Research and Treatment*, vol. 2015, Article ID. 957519, pp. 1-11.

Warren, R. M., et al. (2006) "Differentiation of *Mycobacterium tuberculosis* complex by PCR amplification of genomic regions of difference.", *Int. J. Tub ere. Lung Dis.*, 10(7):818-822 (Jul. 2006).

International Search Report dated Apr. 29, 2019, issued in International Application No. PCT/KR2018/016910, with English Translation.

(Continued)

*Primary Examiner* — Ethan C Whisenant

(74) *Attorney, Agent, or Firm* — Harness, Dickey & Pierce, P.L.C.

(57) ABSTRACT

The present invention relates to a method for determining the presence or absence of *M. tuberculosis*, *M. bovis*, and *M. bovis* BCG in a sample comprising a nucleic acid molecule. A method according to the present invention can detect the individual presence of *M. tuberculosis*, *M. bovis*, and *M. bovis* BCG, and the co-presence of two thereof.

10 Claims, 11 Drawing Sheets

Specification includes a Sequence Listing.

(56) References Cited

OTHER PUBLICATIONS

Costa Pedro et al, "Rapid identification of veterinary-relevantMycobacterium tuberculosiscomplex species using 16S rDNA, IS6110and Regions of Difference-targeted dual labelled hydrolysis probes", Journal of Microbiological Methods, (Sep. 2, 2014), vol. 107, pp. 13-22.

Gordon S V et al, "Identification of Variable Regions in the Genomes of Tubercle Bacili Using Bacterial Artificial Chromosome Arrays", Molecular Microbiology, (May 1, 1999), vol. 32, No. 3, pp. 643-655.

Pounder J I et al, "Mycobacterium tuberculosis complex differentiation by genomic deletion patterns with multiplex polymerase chain reaction and melting analysis", Diagnostic Microbiology and Infectious Disease, vol. 67, No. 1, pp. 101-105.

ESR of European Patent Application No. 18898826.5, dtaed Sep. 14, 2021.

\* cited by examiner

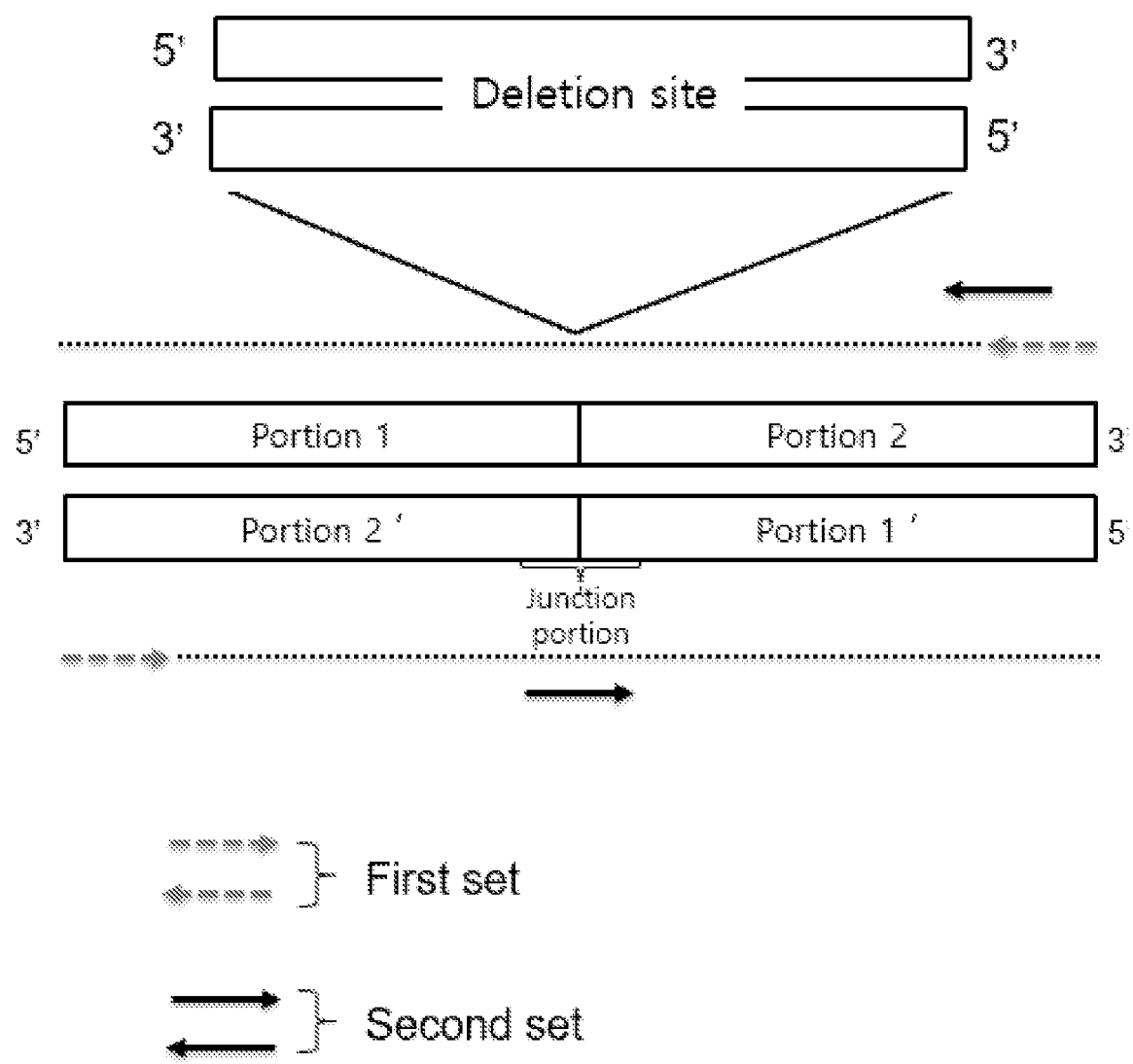

A. Cal Red 610 channel : mpb64

B. Quasar 670 channel : RD9

C. FAM channel : RD1-del

D. HEX channel : RD4-del

A. Cal Red 610 channel: mpb64

B. Quasar 670 channel: RD9

C. FAM channel: RD1-del

D. HEX channel: RD4-del

A. Cal Red 610 channel : mpb64

B. Quasar 670 channel : RD9

C. FAM channel : RD1-del

D. HEX channel : RD4-del

A. Cal Red 610 channel : mpb64

B. Quasar 670 channel : RD9

C. FAM channel : RD1-del

D. HEX channel : RD4-del

A. Cal Red 610 channel : mpb64

C. FAM channel : RD1-del    D. HEX channel : RD4-del

A. Cal Red 610 channel : mpb64

B. Quasar 670 channel : RD9

C. FAM channel : RD1-del

D. HEX channel : RD4-del

A. Cal Red 610 channel : mpb64

B. Quasar 670 channel : RD9

C. FAM channel : RD1-del

D. HEX channel : RD4-del

METHOD FOR DETERMINING THE PRESENCE OR ABSENCE OF M. TUBERCULOSIS, M. BOVIS AND M. BOVIS BCG IN A SAMPLE

CROSS-REFERENCE TO RELATED APPLICATIONS

This application is a national phase application of PCT Application No. PCT/KR2018/016910, filed on 28 Dec. 2018, which claims priority to Korean Patent Application No. 10-2018-0001969, filed on 5 Jan. 2018. The entire disclosures of the applications identified in this paragraph are incorporated herein by references.

BACKGROUND OF THE INVENTION

Field of the Invention

The present invention relates to a method for determining the presence or absence of *M. tuberculosis, M. bovis* and *M. bovis* BCG in a sample comprising nucleic acid molecules.

Description of the Related Art

Generally, pathogens that cause tuberculosis in mammals are collectively called *Mycobacterium tuberculosis* complex (MTBC) and include *Mycobacterium tuberculosis, Mycobacterium africanum, Mycobacterium bovis, Mycobacterium bovis* BCG and *Mycobacterium microti*, etc (O'Reilly L M, et al., a review. Tuber Lung Dis 1995, 76(Suppl 1):S1-S46; Brosch R, et al., Proc Natl Acad Sci USA 2002, 99:3684-3689).

In MTBC, *M. bovis* and *M. tuberculosis* are known as causative agents of tuberculosis in cattle (bovine TB) and humans (human TB), respectively, but *M. bovis* is observed to be transmitted between livestock, between wild animals, and between livestock and wild animals, and from animals to humans or vice versa (Quinn P J, et al., In Clinical Veterinary Microbiology 1994, 156). The human TB *M. tuberculosis* was also reported to be transmitted from humans to cattle.

For tuberculosis treatment, prescription differs from infection with *M. bovis* to infection with *M. tuberculosis* because *M. bovis* is naturally resistant to pyrazinamide (PZA) drug, which is used as a therapeutic agent for *M. tuberculosis* (Konno K, et al., AM ReV Resir Dis 1967, 95:461-469; Morlock G P et al., Antimicrob Agents Chemother 2000, 44: 2291-2295; Scorpio A et al., Nat Med 1996, 2: 662-667).

For this reason, a need exists for the development of a diagnostic method for discriminating individual MTBC pathogens, especially *M. bovis* and *M. tuberculosis.*

Diagnostic methods for bovine tuberculosis developed thus far include intradermal tuberculin test (ITT), Ziehl-Neelsen (ZN) stain, cell culture, polymerase chain reaction (PCR), etc.

ZN stain is fast, but suffers from the problem of lacking specificity and being as low as 50% in sensitivity. The cell culture method also has various problems: tuberculosis bacteria are required to be isolated and culture; it takes 3-4 months to complete the test; and a false negative result is obtained.

Now, most countries take intradermal tuberculin test (ITT) for diagnosis of bovine tuberculosis, but the sensitivity of ITT, although differing depending on reporters, is as low as about 70%, which is in an unsatisfactory level.

In order to overcome problems with such conventional diagnostic method of tuberculosis bacteria, a tuberculosis diagnosis method using PCT technology has been developed which can increases sensitivity and specificity and reduce inspection duration.

However, the genetic homology of 99% or higher between *M. bovis* and *M. tuberculosis* makes molecular biological discrimination therebetween difficult (Brosch R, et al. Proc Natl Acad Sci USA 2002, 99:3684-3689; Gamier T, et al. Proc Natl Acad Sci USA 2003, 100:7877-7882; De la Rua-Domenech R. Tuberculosis (Edinb) 2006, 86:77-109). Further, countries with many tuberculosis cases conduct mandatory vaccination with *M. bovis* BCG, which is a tuberculosis vaccine prepared by attenuating bovine tuberculosis bacteria. However, *M. bovis* BCG is difficult to discriminate from *M. bovis* and *M. tuberculosis*, which may lead to a false positive result upon tuberculosis diagnosis.

Zumarrage M J et al. reported a diagnostic PCR method of discriminating *M. tuberculosis* and *M. bovis* on the basis of a 12.7 kb fragment inserted only into *M. tuberculosis* (Zumarrage M J et al., Microbiology 1999, 145:893-897; Bakshi C S et al., Vet Microbiol 2005, 109:211-216), but the PCR method has difficulty in discriminating *M. bovis* and *M. bovis* BCG.

Therefore, a requirement arises for development of a novel method that can discriminate *M. tuberculosis, M. bovis*, and *M. bovis* BCG with further enhanced sensitivity and specificity.

Throughout the specification, many cited documents and patent documents are referenced and their citations are represented. The disclosures of cited documents and patent documents are entirely incorporated by reference into the present specification, so that the level of the technical field within which the present invention falls, and the details of the present invention are explained more clearly.

SUMMARY OF THE INVENTION

The present inventors have made thorough and intensive efforts to develop a novel method that allows discrimination of *Mycobacterium tuberculosis* (*M. tuberculosis*), *Mycobacterium bovis* (*M. bovis*), and *Mycobacterium bovis* Bacillus Calmette-Guerin (*M. bovis* BCG) in a sample with further improved sensitivity and specificity.

As a result, the present inventors completed a method for determining the individual presence of *M. tuberculosis, M. bovis*, and *M. bovis* BCG and the co-presence of two thereof in a sample by identifying through a nucleic acid amplification whether or not the mpb64 gene exists, whether or not the RD9 (Region of Difference 9) gene exists, whether or not the RD1 (Region of Difference 1) gene is deleted, and whether the RD4 (Region of Difference 4) gene is deleted.

Therefore, an aspect of the present invention is to provide a method for determining the presence or absence of *Mycobacterium tuberculosis, Mycobacterium bovis*, and *Mycobacterium bovis* BCG in a sample comprising nucleic acid molecules.

Another aspect of the present invention is to provide a nucleic acid amplification composition for identifying the presence or absence of *Mycobacterium tuberculosis, Mycobacterium bovis*, and *Mycobacterium bovis* BCG, respectively, in a sample comprising nucleic acid molecules.

Other purposes and advantages of the present invention will be clarified by the following detailed description of the invention, claims, and drawings.

BRIEF DESCRIPTION OF THE DRAWINGS

FIGS. 1A and 1B are schematic diagrams illustrating examples of primer pairs for detecting gene deletions and explaining that the hybridization of the primer pairs and the production of amplicons are dependent on the presence or absence of gene deletions. In FIG. 1B, the primer expressed as an oblique line below the RD1 gene or RD4 gene does not hybridize with the target nucleic acid.

FIGS. 2A and 2B are schematic diagrams illustrating examples of primer pairs and probe sets for detecting gene deletions and explaining that the hybridization of the primer pairs and probe sets and the production of amplicons are dependent on the presence or absence of gene deletions. The probes are "blocked" at the 3'-end to prevent their extension. In FIG. 2B, the probe expressed as an oblique line below the RD1 gene or RD4 gene does not hybridize with the target nucleic acid.

DETAILED DESCRIPTION OF THIS INVENTION

Figure 1B:
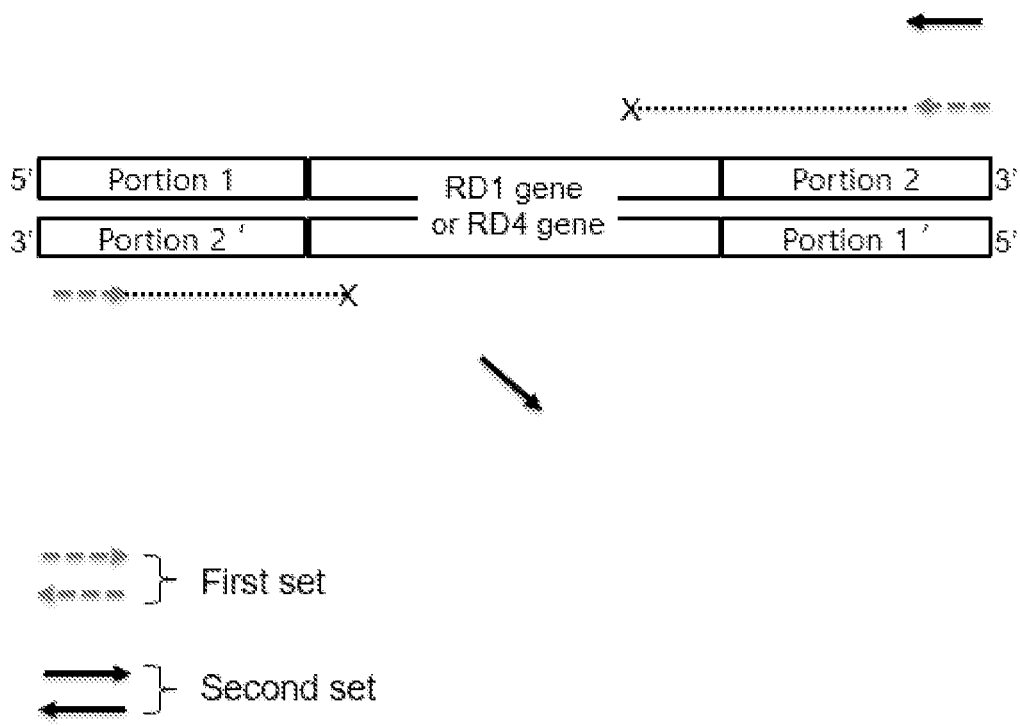

According to one aspect thereof, the present invention provides a method for determining the presence or absence of *Mycobacterium tuberculosis, Mycobacterium bovis*, and *Mycobacterium bovis* BCG in a sample comprising a nucleic acid molecule, the method comprising the steps of:
  a) mixing the sample comprising a nucleic acid molecule with a nucleic acid amplification composition comprising: (i) a pair of primers for detecting an mpb64 gene; (ii) a pair of primers for detecting an RD9 gene; (iii) a pair of primers for detecting an RD1 gene deletion; and (iv) a pair of primers for detecting an RD4 gene deletion, wherein the pair of primers for detecting the mpb64 gene or the RD9 gene allows the production of an amplicon when the mpb64 gene or the RD9 gene is present, and the pair of primers for detecting the RD1 gene deletion or the RD4 gene deletion allows the production of an amplicon when the RD1 gene deletion or the RD4 gene deletion is present;
  (b) performing a nucleic acid amplification reaction;
  (c) determining the presence or absence of the mpb64 gene, the presence or absence of the RD9 gene, the presence or absence of the RD1 gene deletion, and the presence or absence of the RD4 gene deletion on the basis of results of the nucleic acid amplification reaction; and
  (d) determining the presence or absence of *M. tuberculosis, M. bovis*, and *M. bovis* BCG, individually, by using results obtained in step (c).

The present inventors have made thorough and intensive efforts to develop a novel method for discriminating *M. tuberculosis, M. bovis*, and *M. bovis* BCG in a sample with further improved sensitivity and specificity. As a result, the present inventors established a novel protocol that can determine the presence or absence of *M. tuberculosis, M. bovis*, and *M. bovis* BCG, each, in a sample. According to the novel protocol, the presence or absence of an mpb64 gene, the presence or absence of an RD9 gene, the presence or absence of an RD1 gene deletion, and the presence or absence of an RD4 gene deletion can be identified through nucleic acid amplification to determine individual presence of *M. tuberculosis, M. bovis*, and *M. bovis* BCG, and the co-presence of two thereof.

Hereinafter, the present invention will be described in more detail as follows:

Step (a): Mixing a Sample Containing a Nucleic Acid Molecule with Nucleic Acid Amplification Composition According to the present invention, first, a sample comprising a nucleic acid molecule is mixed with a nucleic acid amplification composition comprising:(i) a pair of primers for detecting an mpb64 gene; (ii) a pair of primers for detecting an RD9 gene; (iii) a pair of primers for detecting an RD1 gene deletion; and (iv) a pair of primers for detecting an RD4 gene deletion.

As used herein, the phrase "sample comprising a nucleic acid molecule" means a sample suspected of containing a target nucleic acid molecule therein.

As used herein, the term "nucleic acid" or "nucleic acid molecule" refers to a single-stranded form or double-stranded form of deoxyribonucleotide or ribonucleotide polymer, and the nucleotides include derivatives of naturally occurring nucleotides, non-naturally occurring nucleotides, or modified nucleotides, all of the nucleotides being capable of functioning in the same manner as naturally occurring nucleotides.

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term "sample" as used herein includes biological samples {e.g., cells, tissues and body fluids) and non-biological samples {e.g., food, water, and soil). The biological samples include, without limitation, virus, bacteria, tissue, cell, blood (including whole blood, plasma and serum), lymph, bone marrow fluid, saliva, sputum, swab, aspiration, milk, urine, feces, ocular fluid, semen, brain extracts, spinal cord fluid (SCF), joint fluid, thymic fluid, bronchoalveolar lavage fluid, amniotic fluid, and ascetic fluid. The sample may be subjected to a nucleic acid extraction for an efficient amplification reaction, as well known in the art (see Sambrook, J. et al., Molecular Cloning. A Laboratory Manual, 3rd ed. Cold Spring Harbor Press (2001)). The procedure of nucleic acid extraction may depend on the types of samples. In addition, if the extracted nucleic acid is RNA, it may be further subjected to a reverse transcription for synthesis of cDNA (see Sambrook, 3. et al., Molecular Cloning. A Laboratory Manual, 3rd ed. Cold Spring Harbor Press(2001)).

According to one embodiment of the present invention, the sample may be obtained from a human or a mammal including cattle.

The nucleic acid amplification composition may comprise an oligonucleotide, such as a primer, a probe, etc.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer must be sufficiently long to prime the synthesis of extension products in the presence of the agent for polymerization. The exact length of the primers will depend on many factors, including temperature, application, and source of primer.

The term used herein "probe" refers to a single-stranded nucleic acid molecule comprising a portion or portions that are substantially complementary to a target nucleic acid sequence. According to the present invention, the 3'-end of the probe may be "blocked" to prohibit its extension. The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The primers or probes may be single stranded. The primers or probes include deoxyribonucleotide, ribonucleotide or a combination thereof. The primers or probes used in this invention may be comprised of naturally occurring dNMP (i.e., dAMP, dGM, dCMP and dTMP), modified nucleotide, or non-natural nucleotide.

The sequence of the primer or probe needs not be perfectly complementary to the sequence of a template, but may have a complementarity that allows the primer or probe to be hybridized with the template and to exert its own function.

The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

As used herein, the term, "hybridization" refers to the formation of a double-stranded nucleic acid from two single-stranded polynucleotides through non-covalent binding between complementary nucleotide sequences under predetermined hybridization conditions.

The oligonucleotide (e.g., primer or probe) of the present invention includes a hybridizing nucleotide sequence to a target nucleic acid sequence.

As used herein, the term "a hybridizing nucleotide sequence to a target nucleic acid sequence" means "a nucleotide sequence hybridizing to a target nucleic acid sequence"

According to an embodiment of the present invention, the hybridizing nucleotide sequence of an oligonucleotide (e.g. primer or probe) includes a sequence that can hybridize with a target nucleic acid sequence under a given hybridization condition.

According to an embodiment of the present invention, the oligonucleotide (e.g. primer or probe) comprises a hybridizing nucleotide sequence that can hybridize with a target nucleic acid sequence under a stringent condition.

In an embodiment of the present invention, the stringent condition includes temperature conditions comprising temperatures selected within a certain range around a Tm value of a target sequence with which an oligonucleotide is hybridized, for example, temperatures selected among Tm value ±1° C., ±2° C., ±3° C., ±4° C., ±5° C., and ±7° C.

In an embodiment of the present invention, the stringent condition may comprise the following conditions:
(1) 5×SSC, 5×Denhardt's solution, 0.5% SDS, 50% formamide 32° C., (2) 5×SSC, 5×Denhardt's solution, 0.5% SDS, 50% formamide, 42° C., (3) 5×SSC, 1% SDS, 50 mM Tris-HCl (pH 7.5), 50% formamide 42° C., (4) 5×SSC, 5×Denhardt's solution, 0.5% SDS, 50% formamide 50° C., (5) 0.2×SSC, 0.1% SDS 60° C., (6) 0.2×SSC, 0.1% SDS 62° C., (7) 0.2×SSC, 0.1% SDS 65° C., or (8) 0.1×SSC, 0.1% SDS 65° C., but is not limited thereto.

According to an embodiment of the present invention, the hybridizing nucleotide sequence of the oligonucleotide (e.g. primer or probe) may be determined depending on a hybridization condition used and the nucleic acid sequence to be hybridized with the oligonucleotide etc.

The expression herein that one oligonucleotide "comprises a hybridizing nucleotide sequence" to another oligonucleotide refers to all or a portion of one oligonucleotide has a complementary nucleotide sequence necessary for hybridization with all or a portion of another oligonucleotide.

In the present invention, an oligonucleotide (e.g. primer or probe) may comprise a hybridizing nucleotide sequence complementary to a target nucleic acid sequence.

The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", particularly, perfectly complementary.

The term "substantially complementary" may comprise 1-4 mismatches, 1-3 mismatches or 1-2 mismatches.

When referring to hybridization of a portion of one oligonucleotide to another oligonucleotide, the portion of one oligonucleotide can be regarded as an individual oligonucleotide.

The hybridization may occur when two nucleic acid sequences are perfectly complementary (perfect matched) or substantially complementary with some mismatches (e.g., 1-4 mismatches, 1-3 mismatches or 1-2 mismatches) at a hybridization occurrence site (a double-strand formation site). The degree of complementarity required for hybridization may vary depending on the hybridization reaction conditions, and may be controlled by, particularly, temperature.

For example, the degree of complementarity required for hybridization may be 70% or higher, 75% or higher, 80% or higher, 85% or higher, 90% or higher, or 95% or higher.

According to an embodiment of the present invention, the degree of complementarity or the number of mismatches between two oligonucleotides is determined with reference to a site where hybridization occurs.

In the present, the suitable hybridization conditions or stringent conditions may be routinely determined by optimization procedures. Such procedures are routinely conducted by those skilled in the art to establish protocols for use in a laboratory. For example, conditions such as temperature, concentration of components, hybridization and washing times, buffer components, and their pH and ionic strength may be varied depending on various factors such as the length and GC content of oligonucleotide and target nucleotide sequence. The detailed conditions for hybridization can be found in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999).

As used herein, the terms "hybridization" and "annealing" are not different from each other, and are used interchangeably with each other.

The term "gene deletion", as used herein, is intended to encompass a partial deletion of the gene as well as a whole deletion of the gene.

For example, the term "RD1 gene deletion" may mean a deletion of the entire sequence of the RD1 gene, and also a deletion of the partial sequence of the RD1 gene.

In the present invention, the pair of primers for detection of an mpb64 gene or an RD9 gene allows the production of an amplicon when the gene is present.

According to an embodiment of the present invention, the mpb64 gene, the RD9 gene, the RD4 gene deletion, or the RD1 gene deletion mean a gene or gene deletion existing in at least one of *M. tuberculosis, M. bovis*, or *M. bovis* BCG.

According to an embodiment of the present invention, a sequence of the mpb64 gene, a sequence of the RD9 gene, a sequence of an upstream portion from the 5'-end of a deletion site of the RD4 gene, a sequence of a downstream portion from the 3'-end of a deletion site of the RD4 gene, a sequence of an upstream portion from the 5'-end of a deletion site of the RD1 gene, or a sequence of a downstream portion from the 3'-end of a deletion site of the RD1 gene means a sequence presents in at least one of *M. tuberculosis, M. bovis*, or *M. bovis* BCG.

According to an embodiment of the present invention, the *M. bovis* BCG may be an mpb64 gene-deleted *M. bovis* BCG.

In a specific embodiment of the present invention, the mpb64 gene-deleted *M. bovis* BCG includes *M. bovis* BCG Pasteur, *M. bovis* BCG phipps, *M. bovis* BCG Copenhagen, *M. bovis* BCG Glaxo, and *M. bovis* BCG Tice, but is not limited thereto.

According to an embodiment of the present invention, the primer for detecting an mpb64 gene may comprise a hybridizing nucleotide sequence to an mpb64 gene sequence. Particularly, the primer may comprise a hybridizing nucleotide sequence to an mpb64 gene present in *M. tuberculosis* and *M. bovis*.

According to an embodiment of the present invention, the primer for detecting an RD9 gene may comprise a hybridizing nucleotide sequence to an RD9 gene sequence. Particularly, the primer may comprise a hybridizing nucleotide sequence to an RD9 gene sequence present in *M. tuberculosis*.

In the present invention, the pair of primers for detecting an RD1 gene deletion or an RD4 gene deletion allows the production of an amplicon when the gene is deleted, but does not when the gene is not deleted.

According to an embodiment of the present invention, the primer for detecting an RD1 gene deletion may comprise: (i) a hybridizing nucleotide sequence to an upstream portion from the 5'-end of a deletion site of the RD1 gene; (ii) a hybridizing nucleotide sequence to a downstream portion from the 3'-end of the deletion site of the RD1 gene; or (iii) a hybridizing nucleotide sequence to a junction portion formed by deletion of the RD1 gene.

According to an embodiment of the present invention, the primer for detecting an RD4 gene deletion may comprise: (i) a hybridizing nucleotide sequence to an upstream portion from the 5'-end of a deletion site of the RD4 gene, (ii) a hybridizing nucleotide sequence to a downstream portion from the 3'-end of the deletion site of the RD4 gene, or (iii) a hybridizing nucleotide sequence to a junction portion formed by deletion of the RD4 gene.

The term "site", as used with referring to gene deletion site herein, is intended to encompass multiple nucleotides as well as a single nucleotide. For instance, the deletion site may have a length of 700 bp or more, 1,000 bp or more, 1,500 bp or more, 2,000 bp or more, 2,500 bp or more, 3,000 bp or more, 4,000 bp or more, 5,000 bp or more, 6,000 bp or more, 7,000 bp or more, 8,000 bp or more, 9,000 bp or more, 10,000 bp or more, or 20,000 bp or more.

According to an embodiment of the present invention, the deletion site may have a length of 2,000 bp-25,000 bp, 5,000 bp-20,000 bp, 7,000 bp-15,000 bp, or 9,000 bp-13,000 bp.

As used herein, the term "an upstream portion from the 5'-end of a deletion site of a particular gene" refers to a portion upstream from and adjacent to the 5'-end of a deletion site of a particular gene. For a double strand, a portion upstream from and adjacent to the 5'-end of a deletion site of a particular gene includes both a portion 1 located upstream from the 5'-end on one strand and a portion 1' located upstream from the 5'-end on the other strand (see FIGS. 1A and 1B).

As used herein, the term "a downstream portion from the 3'-end of a deletion site of a particular gene" refers to a portion downstream from and adjacent to the 3'-end of a deletion site of a particular gene. For a double strand, a portion downstream from and adjacent to the 3'-end of a deletion site of a particular gene includes both a portion 2 located downstream from the 3'-end on one strand and a portion 2' located downstream from the 3'-end on the other strand (see FIGS. 1A and 1B).

As used herein, the term "junction portion" refers to a portion formed by joining an upstream portion from the 5'-end of the deletion site to a downstream portion from the 3'-end of the deletion site, when the deletion site of a target gene is deleted. The junction portion includes a position at which an upstream portion from the 5'-end and a downstream portion from the 3'-end of the deletion site are joined to each other. Particularly, the junction portion includes a part of the upstream portion from the 5'-end and a part of the downstream portion from the 3'-end of a deletion site.

According to an embodiment of the present invention, a sequence of the junction portion has a length of 200 bp or less, 150 bp or less, 100 bp or less, 70 bp or less, 60 bp or less, 50 bp or less, 40 bp or less, or 30 bp or less.

According to an embodiment of the present invention, a sequence of the junction portion has a length of 5 bp or more, 10 bp or more, 15 bp or more, 20 bp or more, 25 bp or more, or 30 bp or more.

According to an embodiment of the present invention, the part of the upstream portion from the 5'-end of the junction portion has a length of 100 bp or less, 70 bp or less, 60 bp or less, 50 bp or less, 40 bp or less, 30 bp or less, 25 bp or less, 20 bp or less, 15 bp or less, 10 bp or less, or 5 bp or less.

According to an embodiment of the present invention, the part of the upstream portion from the 5'-end of the junction portion has a length of 3 bp or more, 5 bp or more, 10 bp or more, 15 bp or more, or 20 bp or more.

According to an embodiment of the present invention, the part of the downstream portion from the 3'-end of the junction portion has a length of 100 bp or less, 70 bp or less, 60 bp or less, 50 bp or less, 40 bp or less, 30 bp or less, 25 bp or less, 20 bp or less, 15 bp or less, 10 bp or less, or 5 bp or less.

According to an embodiment of the present invention, the part of the downstream portion from the 3'-end of the junction portion has a length of 3 bp or more, 5 bp or more, 10 bp or more, 15 bp or more, or 20 bp or more.

According to an embodiment of the present invention, a primer or probe hybridizing with the junction portion comprises a hybridizing nucleotide sequence to both a part of the upstream portion from the 5'-end and a part of the downstream portion from the 3'-end of the deletion site.

According to an embodiment of the present invention, the upstream portion from the 5'-end of a deletion site of a particular gene may be (i) a portion within 1000 bp or less, 800 bp or less, 600 bp or less, 500 bp or less, 400 bp or less, 300 bp or less, or 200 bp or less upstream from the 5'-end of the deletion site of the particular gene, or (ii) a portion within 1000 bp or less, 800 bp or less, 600 bp or less, 500 bp or less, 400 bp or less, 300 bp or less, or 200 bp or less upstream from the 5'-end of the junction portion.

According to an embodiment of the present invention, the downstream portion from the 3'-end of a deletion site of a particular gene may be (i) a portion within 1000 bp or less, 800 bp or less, 600 bp or less, 500 bp or less, 400 bp or less, 300 bp or less, or 200 bp or less downstream from the 3'-end of the deletion side of the particular gene or (ii) a portion within 1000 bp or less, 800 bp or less, 600 bp or less, 500 bp or less, 400 bp or less, 300 bp or less, or 200 bp or less downstream from the 3'-end of the junction portion.

According to an embodiment of the present invention, a sequence of the upstream portion from the 5'-end of deletion site of an RD1 gene may comprise a sequence selected from the group consisting of the sequence of SEQ ID NO: 1, the sequence of SEQ ID NO: 2, and a sequence having a homology of 80% or higher thereto, and a sequence of the downstream portion from the 3'-end of a deletion site of the RD1 gene may comprise a sequence selected from the group consisting of the sequence of SEQ ID NO: 3, the sequence of SEQ ID NO: 4, and a sequence having a homology of 80% or higher thereto.

According to an embodiment of the present invention, a sequence of the upstream portion from the 5'-end of deletion site of an RD4 gene may comprise a sequence selected from the group consisting of the sequence of SEQ ID NO: 5, the sequence of SEQ ID NO: 6, and a sequence having a homology of 80% or higher thereto, and a sequence of the downstream portion from the 3'-end of a deletion site of the RD4 gene may comprise a sequence selected from the group consisting of the sequence of SEQ ID NO: 7, the sequence of SEQ ID NO: 8, and a sequence having a homology of 80% or higher thereto.

According to an embodiment, a pair of primers for detecting a particular gene (e.g., RD1 gene or RD4 gene) deletion may be designed such that one primer comprises a hybridizing nucleotide sequence to an upstream portion from the 5'-end of a deletion site of a particular gene while the other comprises a hybridizing nucleotide sequence to a downstream portion from the 3'-end of a deletion site of a particular gene.

As such, a pair of primers for detecting a particular gene deletion can specifically hybridize with an upstream portion from the 5'-end and a downstream portion from the 3'-end of the deletion site of the particular gene irrespective of the presence or absence of a particular gene deletion. However, the production of an amplicon can be controlled by taking advantage of a difference in template length according to the presence or absence of a deletion.

For example, a template may be far longer when a particular gene is not deleted than is deleted. Adjustment of an extension time or amplification condition may allow the production of relatively short amplicons, without generating a relatively long amplicon. In the present invention, an amplicon is produced in the case where a particular gene is deleted (first set in FIG. 1A) and an amplicon is not produced in the case where a particular gene is not deleted (first set in FIG. 1B).

According to an embodiment of the present invention, a target portion to be hybridized with a pair of primers for detecting a gene deletion is determined such that an amplicon cannot be produced in the case where a gene is not deleted, but can be produced in the case where a gene is deleted under a predetermined amplification condition (e.g. comprising an adjusted primer extension time)

According to another embodiment of the present invention, a pair of primers for detecting a gene deletion may be designed such that one primer comprises a hybridizing nucleotide sequence to a junction portion formed by deletion of a particular gene and the other primer comprises a hybridizing nucleotide sequence to an upstream portion from the 5'-end or a downstream portion from the 3'-end of a deletion site of a particular gene. The designed pair of primers does not allow the production of an amplicon when a particular gene is not deleted because primer hybridization does not occur due to the lack of the junction portion (second set in FIG. 1B). In contrast, when a particular gene is deleted, the designed pair of primers can allow the production of an amplicon because the junction portion is present at which the primer hybridization occurs (second set in FIG. 1A).

According to a specific embodiment of the present invention, the primer for detecting an mpb64 gene may comprise a hybridizing nucleotide sequence to a sequence selected from the group consisting of the sequence of SEQ ID NO: 9, the sequence of SEQ ID NO: 10, and a complementary sequence thereto.

According to a specific embodiment of the present invention, the primer for detecting an RD9 gene may comprise a hybridizing nucleotide sequence to a sequence selected from the group consisting of the sequence of SEQ ID NO: 11, the sequence of SEQ ID NO: 12, and a complementary sequence thereto.

According to a specific embodiment of the present invention, the primer for detecting an RD1 gene deletion may comprise a hybridizing nucleotide sequence to a sequence selected from the group consisting of the sequence of SEQ ID NO: 13, the sequence of SEQ ID NO: 14, and a complementary sequence thereto.

According to a specific embodiment of the present invention, the primer for detecting an RD4 gene deletion may comprise a hybridizing nucleotide sequence to a sequence selected from the group consisting of the sequence of SEQ ID NO: 15, the sequence of SEQ ID NO: 16, and a complementary sequence thereto.

Step (b): Nucleic Acid Amplification Reaction

The amplification of a target nucleic acid molecule may be performed by various primer-involved nucleic acid amplification methods known in the art. Specifically, the amplification of a target nucleic acid is performed according to polymerase chain reaction (PCR), which is disclosed in U.S. Pat. Nos. 4,683,195, 4,683,202, and 4,800,159. Other examples are ligase chain reaction (LCR, U.S. Pat. Nos. 4,683,195 and 4,683,202; and PCR Protocols: A Guide to Methods and Applications (Innis et al., eds, 1990)), strand displacement amplification (SDA, Walker, et al. Nucleic Acids Res. 20(7):1691-6 (1992); and Walker PCR Methods Appl. 3(1):1-6 (1993)), transcription-mediated amplification (Phyffer, et al., J. Clin. Microbiol. 34:834-841 (1996); and Vuorinen, et al., J. Clin. Microbiol. 33:1856-1859 (1995)), nucleic acid sequence-based amplification (NASBA, Compton, Nature 350(6313):91-2 (1991)), rolling circle amplification (RCA, Lisby, Mol. Biotechnol. 12(1):75-99 (1999); and Hatch et al., Genet. Anal. 15(2):35-40 (1999)), and Q-Beta Replicase (Lizardi et al., BiolTechnology 6:1197 (1988)).

According to an embodiment of the present invention, a polymerase chain reaction (PCR) may be performed under an reaction condition for amplifying the nucleic acid amplification composition mixed with the sample comprising a nucleic acid molecule in step (a).

According to an embodiment of the present invention, the PCR is performed under a suitable condition where the pair of primers comprised in the nucleic acid amplification composition allows the production of an amplicon.

PCR is widely used for amplification of nucleic acid molecules in relevant fields and includes repetitive cycles of denaturation of a target nucleic acid molecule, annealing (hybridization) to the target nucleic acid sequence, and extension of a primer (U.S. Pat. Nos. 4,683,195, 4,683,202, and 4,800,159; and Saiki et al., (1985) Science 230, 1350-1354).

Where the target nucleic acid molecule is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

In one embodiment of the present invention, the annealing (hybridization) step is conducted under a hybridization condition where the primer or probe can selectively hybridize with a target nucleic acid sequence, especially under a stringent condition.

As used herein, the term, "stringent conditions" refers to conditions under which a probe, primer or oligonucleotide will hybridize to its target sequence, but to no other sequences.

In an embodiment of the present invention, the stringent condition includes temperature conditions comprising temperatures selected within a certain range around a Tm value between an oligonucleotide and a target nucleic acid sequence, for example, temperatures selected among Tm value $\pm 1°$ C., $\pm 2°$ C., $\pm 3°$ C., $\pm 4°$ C., $\pm 5°$ C., and $\pm 7°$ C.

The primer annealed to the target sequence is extended by a template-dependent polymerase, including "Klenow" fragment of E. coli DNA polymerase I, a thermostable DNA polymerase, and bacteriophage T7 DNA polymerase. In an embodiment, the template-dependent polymerase is a thermostable DNA polymerase obtained from a variety of bacterial species, including Thermus aquaticus (Taq), Thermus thermophilus (Tth), Thermus filiformis, Thermis flavus, Thermococcus literalis, Thermus antranikianii, Thermus caldophllus, Thermus chliarophllus, Thermus flavus, Thermus igniterrae, Thermus lacteus, Thermus oshimai; Thermus ruber, Thermus rubens, Thermus scotoductus, Thermus silvans, Thermus species Z05, Thermus species sps 17, Thermus thermophilus, Thermotoga maritima, Thermotoga neapolitana, Thermosipho africanus, Thermococcus Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifex pyrophllus and Aquifex aeolieus. Most preferably, the template-dependent nucleic acid polymerase is Taq polymerase.

For PCR, components necessary for the reaction may be provided in excess in the reaction vessel. Excess in reference to components of the extension reaction refers to such a sufficient amount of each component as not to substantially limit the ability of the component to achieve a desired extent of extension. For a desired reaction, it is desirable that dATP, dCTP, dGTP, and dTTP, and necessary cofactors such as $Mg^{2+}$ are provided in sufficient quantities to the reaction mixture.

Step (C): Determination of Presence or Absence of Gene or Gene Deletion

The presence or absence of the mpb64 gene, the RD9 gene, the RD1 gene deletion, or the RD4 gene deletion is determined from the nucleic acid amplification results in step (b).

According to an embodiment of the present invention, the presence or absence of the mpb64 gene, the RD9 gene, the RD1 gene deletion, or the RD4 gene deletion may be determined by detecting the amplicon.

According to an embodiment of the present invention, the presence or absence of the mpb64 gene and the RD9 gene may be determined by detecting respective amplicons indicating the presence of the genes.

According to an embodiment of the present invention, the presence or absence of the RD1 gene deletion and the RD4 gene deletion may be determined by detecting respective amplicons indicating the gene deletions.

According to an embodiment, the amplicon may have a length of 10 bp-5,000 bp, 50 bp-3,000 bp, 100 bp-2,000 bp, 150 bp-1,000 bp, or 200 bp-600 bp.

According to an embodiment of the present invention, the pair of primers may determine a hybridization position allowing the production of an amplicon 10 bp-5,000 bp, 50 bp-3,000 bp, 100 bp-2,000 bp, 150 bp-1,000 bp, or 200 bp-600 bp in length.

According to an embodiment of the present invention, the detection of the amplicon may be performed in a post-amplification detection manner or in a real-time detection manner.

The post-amplification detection manner is a method whereby amplicons are detected after the amplification of nucleic acids. The post-amplification detection manner includes, for example, the separation of amplicons according to size difference (e.g., electrophoresis) or the separation of amplicons through immobilization, but is not limited thereto.

Alternatively, for the post-amplification detection manner, post-PCR melting analysis may be used in which, after the amplification of a target nucleic acid sequence, the fluorescence intensity is monitored while the temperature is raised or lowered in a certain period, and then amplicons are detected by melting profiles (U.S. Pat. Nos. 5,871,908 and 6,174,670, and WO 2012/096523).

The real-time detection manner is a method whereby a target nucleic acid sequence may be detected while the amplification of the target nucleic acid is monitored in real time. For detection of a target nucleic acid sequence, a signal can be detected at one or more temperatures during the reaction, for example, at one temperature or at two temperatures.

The post-amplification manner or the real-time detection manner may use a label or a labeled oligonucleotide for providing a signal depending on the presence of a nucleic acid to be detected.

For example, the detection may be performed using a non-specific fluorescence dye that non-specifically intercalates into a duplex.

In addition, a labeled primer or probe may be used.

Examples of methods of using a labeled primer include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 Aug. 1999, and U.S. Pat. No. 6,326,145), and TSG Primer method (WO 2011/078441).

Examples of methods of using a labeled probe include a molecular beacon method using a dual-labeled probe forming a hair-pin structure (Tyagi et al, Nature Biotechnology v. 14 Mar. 1996), a hybridization probe method using two probes single-labeled with a donor or an acceptor (Bernad et al, 147-148 Clin Chem 2000; 46), a Lux method using a single-labeled oligonucleotide (U.S. Pat. No. 7,537,886), and a TaqMan method using a cleavage reaction of the double-labeled probe by 5'-nuclease activity of DNA polymerase as well as the hybridization of a dual-labeled probe (U.S. Pat. Nos. 5,210,015 and 5,538,848), but are not limited thereto.

In addition, the detection may be performed using a duplex formed depending on the presence of the target nucleic acid sequence. The duplex formed depending on the presence of the target nucleic acid sequence is not an amplicon itself of the target sequence formed by the amplification reaction, and the amount of the duplex increases in proportion to the amplification of the target nucleic acid sequence.

The duplex formed depending on the presence of the target nucleic acid sequence may be obtained according to various method, for example, Invader assay (U.S. Pat. Nos. 5,691,142, 6,358,691, and 6,194,149), PTOCE (PTO Cleavage and Extension) method (WO 2012/096523), PCEC (PTO Cleavage and Extension-dependent Cleavage) method (WO 2012/134195), PCE-SH (PTO Cleavage and Extension-dependent Signaling Oligonucleotide Hybridization) method (WO 2013/115442), PCE-SC (PTO Cleavage and Extension-dependent Signaling Oligonucleotide Cleavage) method (WO 2013/157821), PCE-NH (PTO Cleavage and Extension-dependent Non-Hybridization) method (WO 2014/104818), PCE-IH (PTO Cleavage and Extension-dependent Immobilized Oligonucleotide Hybridization) method (WO 2015/008985), and CCTF(Cleaved Complementary Tag Fragment) method (WO2017/188669), the contents of which are incorporated herein by reference.

According to an embodiment of the present invention, the duplex formed depending on the presence of the target nucleic acid sequence may be formed depending on the cleavage of the probe or the primer.

In addition, for the real-time detection, a method of detecting at least one target nucleic acid sequence through only a single type of label using signal detection at different temperatures may be employed. The techniques therefor are disclosed in WO 2015/147412, WO 2016/093619, and WO 2016/093620, the contents of which are incorporated herein by reference.

According to an embodiment of the present invention, the nucleic acid amplification composition may further comprise (i) a probe for detecting an mpb64 gene, (ii) a probe for detecting an RD9 gene, (iii) a probe for detecting an RD1 gene deletion, or (iv) a probe for detecting an RD4 gene deletion.

Each of the probes may comprise a hybridizing nucleotide sequence to an amplicon to be detected. With respect to the disclosure of the probes, reference may be made to the foregoing disclosure on the primers.

According to an embodiment of the present invention, the probe for detecting an mpb64 gene may comprise a hybridizing nucleotide sequence to an mpb64 gene sequence.

According to a specific embodiment of the present invention, the probe for detecting an mpb64 gene may comprise a hybridizing nucleotide sequence to a sequence selected from the group consisting of the sequence of SEQ ID NO: 17 and a complementary sequence thereto.

According to an embodiment of the present invention, the probe for detecting an RD9 gene may comprise a hybridizing nucleotide sequence to an RD9 gene sequence.

According to a specific embodiment, the probe for detecting an RD9 gene may comprise a hybridizing nucleotide sequence to a sequence selected from the group consisting of the sequence of SEQ ID NO: 18 and a complementary sequence thereto.

According to an embodiment of the present invention, the probe for detecting an RD1 gene deletion may comprise: (i) a hybridizing nucleotide sequence to an upstream portion from the 5'-end of a deletion site of the RD1 gene, (ii) a hybridizing nucleotide sequence to a downstream portion from the 3'-end of a deletion site of the RD1 gene, or (iii) a hybridizing nucleotide sequence to a junction portion formed by deletion of the RD1 gene.

According to an embodiment of the present invention, the probe for detecting an RD4 gene deletion may comprise: (i) a hybridizing nucleotide sequence to an upstream portion from the 5'-end of a deletion site of the RD4 gene, (ii) a hybridizing nucleotide sequence to a downstream portion from the 3'-end of a deletion site of the RD4 gene, or (iii) a hybridizing nucleotide sequence to a junction portion formed by deletion of the RD4 gene.

According to an embodiment of the present invention, a probe for detecting a particular gene deletion(e.g., RD1 gene deletion or RD4 gene deletion) may be designed to comprise a hybridizing nucleotide sequence to an upstream portion from the 5'-end of a deletion site of a particular gene, or a hybridizing nucleotide sequence to a downstream portion from the 3'-end of a deletion site of a particular gene. The probe can specifically hybridize with the upstream portion from the 5'-end or the downstream portion from the 3'-end of deletion site of the particular gene irrespective of the presence of a particular gene deletion. Particularly, when a method for generating signal using the probe cleavage by extension of primer(e.g., TaqMan method etc.) or a method for generating signal using duplex formed depending on the probe cleavage by extension of primer (e.g., Invader method, PTOCE method, etc.) is used, of a pair of primers for detecting a particular gene deletion, one primer having the same orientation as the probe may be designed to comprise a hybridizing nucleotide sequence to a portion different from that for the probe. In such a case, adjusting an amplification reaction time, particularly primer extension time can control the cleavage of the probe by the primer extension depending on the presence or absence of a gene deletion. For example, a primer extension time may be adjusted such that when the particular gene is deleted, the extension time is sufficiently long for the primer to be extended to a portion which the probe is hybridized with and thus cleave the probe (first set in FIG. 2A) but when the particular gene is not deleted, the extension time is short for the primer to extend to the portion so that the probe is not cleaved (first set in FIG. 2B).

Figure 2A:
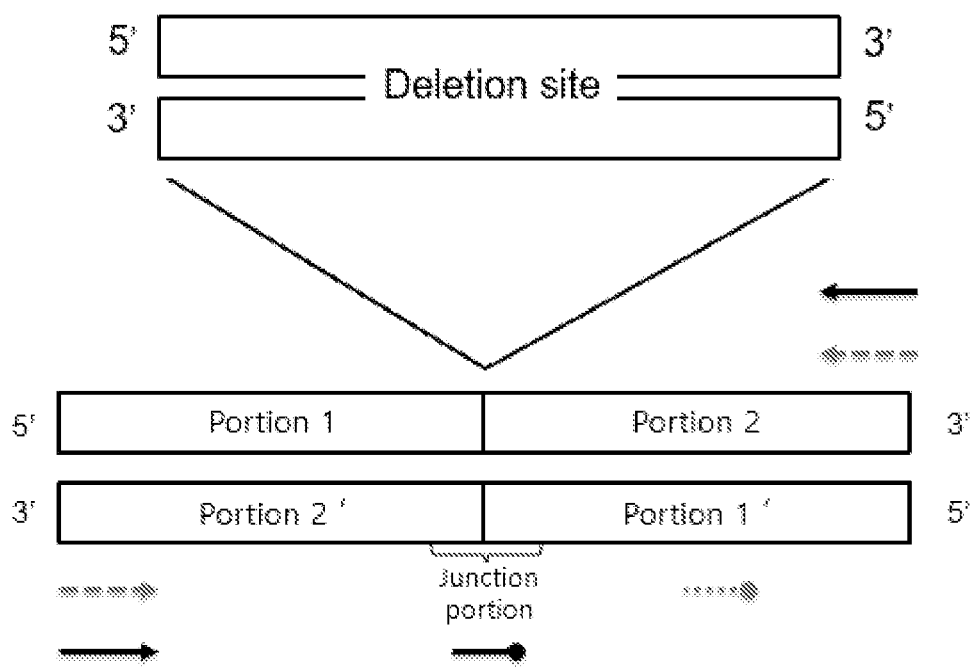
Figure 2B:
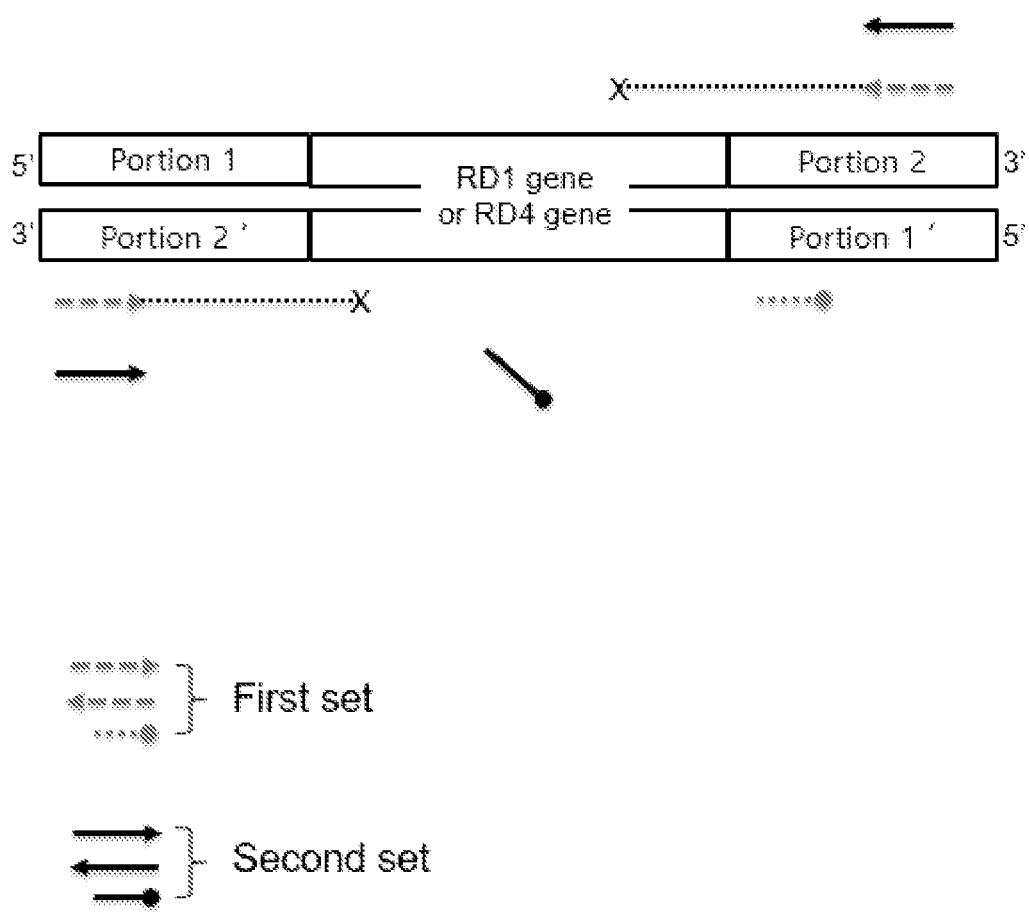

In a specific embodiment of the present invention, when the primer and the probe for detecting an RD1 gene deletion comprise a hybridizing nucleotide sequence to the upstream portion from the 5'-end of a deletion site of the RD1 gene or to a downstream portion from the 3'-end of a deletion site of the RD1 gene, the probe and one primer of the pair of primers, which has the same orientation as the probe, comprise hybridizing nucleotide sequences to different portions from each other (FIG. 2A). In other words, the probe comprises hybridizing nucleotide sequences to one of the two portions and one primer of the pair of primers which has the same orientation as the probe comprises hybridizing nucleotide sequences to the other of the two portions.

In a specific embodiment of the present invention, when the primer and the probe for detecting an RD4 gene deletion includes a hybridizing nucleotide sequence to the upstream portion from the 5'-end of an RD4 gene deletion or an downstream portion from the 3'-end of a deletion site of the RD4 gene, the probe and one primer of the pair of primers, which has the same orientation as the probe, comprise hybridizing nucleotide sequences to different portions from each other (FIG. 2A). In other words, the probe comprises hybridizing nucleotide sequences to one of the two portions and one primer of the pair of primers which has the same orientation as the probe comprises hybridizing nucleotide sequences to the other of the two portions.

According to another embodiment of the present invention, a probe for detecting a particular gene deletion may be designed to comprise a hybridizing nucleotide sequence to a junction portion formed by deletion of a particular gene. The designed probe does not hybridize with the target template when a particular gene is not deleted because of the lack of the junction portion. In contrast, when a particular gene is deleted, the designed probe can hybridize with the junction portion because the junction portion is formed.

According to a specific embodiment of the present invention, the probe for detecting an RD1 gene deletion may include a hybridizing nucleotide sequence to a sequence selected from the group consisting of the sequence of SEQ ID NO: 19 and a complementary sequence thereto.

According to a specific embodiment of the present invention, the probe for detecting an RD4 gene deletion may include a hybridizing nucleotide sequence to a sequence selected from the group consisting of the sequence of SEQ ID NO: 20 and a complementary sequence thereto.

According to an embodiment of the present invention, the nucleic acid amplification composition may further comprise a pair of primers for detecting a gene for screening *M. tuberculosis*, *M. bovis*, and *M. bovis* BCG. The screening gene includes a gene present in all of *M. tuberculosis*, *M. bovis*, and *M. bovis* BCG, for example, mpb70 and IS6110, but is not limited thereto.

According to another embodiment of the present invention, the nucleic acid amplification composition may further a probe for detecting a gene for screening *M. tuberculosis*, *M. bovis*, and *M. bovis* BCG.

In a specific embodiment of the present invention, the gene for screening *M. tuberculosis*, *M. bovis*, and *M. bovis* BCG may be mpb70.

Step (d) Determination of Presence or Absence of *M. tuberculosis*, *M. bovis*, and *M. bovis* BCG Using the results determined in step (c) with respect to the presence or absence of an mpb64 gene, the presence or absence of an RD9 gene, the presence or absence of an RD1 gene deletion, and the presence or absence of an RD4 gene deletion, the presence or absence of each of *M. tuberculosis*, *M. bovis*, and *M. bovis* BCG is determined.

In the present invention, among genes in which *M. tuberculosis*, *M. bovis*, and *M. bovis* BCG are different from one another due to deletion or insertion, an RD9 gene, an RD4 gene, an RD1 gene, and an mpb64 gene were selected because an RD9 gene is retained by *M. tuberculosis* alone, an RD4 gene is deleted in only *M. bovis* and *M. bovis* BCG, an RD1 gene is deleted in *M. bovis* BCG alone, and an mpb64 gene is deleted in only *M. bovis* BCG (Table 1). According to the method of the present invention, a combination of the presence or absence of an mpb64 gene, the presence or absence of an RD9 gene, the presence or absence of an RD1 gene deletion, and the presence or absence of an RD4 gene deletion can be used to determine the presence or absence of *M. tuberculosis*, *M. bovis*, and *M. bovis* BCG.

In Table 1, the presence or absence of the mpb64 gene, RD1 gene, RD4 gene, and RD9 gene in pathogens *M. tuberculosis*, *M. bovis*, and *M. bovis* BCG is summarized.

TABLE 1

|  | mpb64 | RD1 | RD4 | RD9 |
|---|---|---|---|---|
| *M. tuberculosis* | ○ | ○ | ○ | ○ |
| *M. bovis* | ○ | ○ | X | X |
| *M. bovis* BCG | X | X | X | X |

○: gene present; X: gene absent (i.e., gene deleted)

In the method of the present invention, the reproducibility of results with respect to the presence or absence of the genes or gene deletion may be decreased for a sample that has a nucleic acid molecule concentration lower than the limit of detection (LoD), which is the lowest quantity of a substance (e.g., a nucleic acid molecule) that can be detectable. For example, although a gene or a gene deletion is present, determination may be made of the absence of the gene or gene deletion. Such poor reproducibility with respect to the presence of a gene or gene deletion may have a great influence on the final determination of the presence or absence of pathogens.

In an embodiment of the present invention, in order to avoid such problems (i.e., determination of the absence of pathogens in spite of the presence thereof), the presence or absence of *M. tuberculosis*, *M. bovis*, and *M. bovis* BCG can be determined on the basis of the presence or absence of some genes or some gene deletion.

According to an embodiment of the present invention, *M. tuberculosis* is determined to be present in the sample if the presence of the RD9 gene is determined, in step (d). According to another embodiment of the present invention, the combination of the presence of the mpb64 gene, the absence of RD1 gene deletion, the absence of RD4 gene deletion, and the presence of the RD9 gene represents the presence of *M. tuberculosis* alone, however, the presence of *M. tuberculosis* alone can be determined irrespective of determination of the presence or absence of the mpb64 gene because the combination of the absence of RD1 gene deletion, the absence of RD4 gene deletion, and the presence of the RD9 gene is discriminated from criteria for determination of the infection of the other pathogens.

According to an embodiment of the present invention, *M. bovis* is determined to be present in the sample if the presence of the mpb64 gene, the absence of the RD1 gene deletion, and the presence of the RD4 gene deletion are determined, in step (d).

According to an embodiment of the present invention, *M. bovis* BCG is determined to be present in the sample if the absence of the mpb64 gene and the presence of the RD1 gene deletion are determined, in step (d). According to another embodiment of the present invention, the combination of the absence of the mpb64 gene, the absence of RD1 gene deletion, the absence of RD4 gene deletion, and the absence of the RD9 gene represents the presence of *M. bovis* BCG alone, however, the presence of *M. bovis* BCG alone can be determined irrespective of determination of the presence or absence of the RD4 gene deletion because the combination of the absence of the mpb64 gene, the presence of RD1 gene deletion, and the absence of the RD9 gene is discriminated from criteria for determination of the infection of the other pathogens.

In addition, According to another embodiment of the present invention, the combination of the presence of the mpb64 gene, the presence of RD1 gene deletion, the presence of RD4 gene deletion, and the presence of the RD9 gene represents the presence of both *M. tuberculosis* and *M. bovis* BCG, however, the presence of both *M. tuberculosis* and *M. bovis* BCG can be determined irrespective of determination of the presence or absence of the mpb64 gene and the presence or absence of the RD4 gene deletion because the combination of the presence of RD1 gene deletion and the presence of the RD9 gene is discriminated from criteria for determination of the infection of the other pathogens.

According to an embodiment of the present invention, criteria for determining single infection or co-infection according to the presence or absence of the mpb64 gene and the RD9 gene and the presence or absence of RD1 gene deletion and RD4 gene deletion are listed in Table 2.

TABLE 2

| | Mpb64 | RD1 deletion | RD4 deletion | RD9 |
|---|---|---|---|---|
| *M. tuberculosis* | +/− | − | − | + |
| *M. bovis* | + | − | + | − |
| *M. bovis* BCG | − | + | +/− | − |
| *M. bovis* + *M. bovis* BCG | + | + | + | − |
| *M. tuberculosis* + *M. bovis* | + | − | + | + |
| *M. tuberculosis* + *M. bovis* BCG | +/− | + | +/− | + |

+: presence; −: absence; +/−: presence or absence

According to a specific embodiment of the present invention, *M. tuberculosis* is determined to be present alone in the sample if the absence of the RD1 gene deletion, the absence of the RD4 gene deletion, and the presence of the RD9 gene are determined, in step (d).

According to a further specific embodiment of the present invention, *M. tuberculosis* is determined to be present alone in the sample if the presence of the mpb64 gene, the absence of the RD1 gene deletion, the absence of the RD4 gene deletion, and the presence of the RD9 gene are determined, in step (d).

According to a specific embodiment of the present invention, *M. bovis* is determined to be present alone in the sample if the presence of the mpb64 gene, the absence of the RD1 gene deletion, the presence of the RD4 gene deletion, and the absence of the RD9 gene are determined, in step (d).

According to a specific embodiment of the present invention, *M. bovis* BCG is determined to be present alone in the sample if the absence of the mpb64 gene, the presence of the RD1 gene deletion, and the absence of the RD9 gene are determined, in step (d).

According to a further specific embodiment of the present invention, *M. bovis* BCG is determined to be present alone in the sample if the absence of the mpb64 gene, the presence of the RD1 gene deletion, the presence of the RD4 gene deletion, and the absence of the RD9 gene are determined, in step (d).

In Table 2, criteria for co-infection may be obtained by combining criteria for single infections. For co-infection with *M. bovis*, and *M. bovis* BCG, by way of example, a criterion for the presence (+) of the mpb64 gene results from a combination of the presence (+) of the mpb64 gene, which is the criterion for single infection with *M. bovis*, and the absence (−) of the mpb64 gene, which is the criterion for single infection with *M. bovis* BCG.

According to a specific embodiment of the present invention, *M. bovis* and *M. bovis* BCG are determined to be simultaneously present in the sample if the presence of the mpb64 gene, the presence of the RD1 gene deletion, the presence of the RD4 gene deletion, and the absence of the RD9 gene are determined, in step (d).

According to a specific embodiment of the present invention, *M. bovis* and *M. tuberculosis* are determined to be simultaneously present in the sample if the presence of the mpb64 gene, the absence of the RD1 gene deletion, the presence of the RD4 gene deletion, and the presence of the RD9 gene are determined, in step (d).

According to a specific embodiment of the present invention, *M. bovis* BCG and *M. tuberculosis* are determined to be simultaneously present in the sample if the presence of the RD1 gene deletion and the presence of the RD9 gene are determined, in step (d).

According to a further specific embodiment of the present invention, *M. bovis* BCG and *M. tuberculosis* are determined to be simultaneously present in the sample if the presence of the mpb64 gene, the presence of the RD1 gene deletion, the presence of the RD4 gene deletion, and the presence of the RD9 gene are determined, in step (d).

The method of the present invention does not distinguish co-infection with *M. tuberculosis* and *M. bovis* BCG and triple infection with *M. tuberculosis, M. bovis*, and *M. bovis* BCG.

According to an embodiment of the present invention, when *M. bovis* BCG and *M. tuberculosis* are determined to be simultaneously present in the sample, particularly, by the combination of the presence of the mpb64 gene, the presence of RD1 gene deletion, the presence of RD4 gene deletion, and the presence of the RD9 gene, *M. bovis* may be present in the sample.

Unless otherwise defined in the present specification, all technical and scientific terms used herein have the same meaning as commonly understood by those skilled in the art.

The another aspect of the present invention provides a nucleic acid amplification composition for identifying the presence or absence of *Mycobacterium tuberculosis, Mycobacterium bovis*, and *Mycobacterium bovis* BCG, respectively, in a sample comprising nucleic acid molecules, the composition comprising:

(a) a pair of primers for detecting an mpb64 gene;

(b) a pair of primers for detecting an RD9 gene;

(c) a pair of primers for detecting an RD1 gene deletion; and (d) a pair of primers for detecting an RD4 gene deletion.

Since the nucleic acid amplification composition for identifying the presence or absence of *Mycobacterium tuberculosis, Mycobacterium bovis*, and *Mycobacterium bovis* BCG, respectively of this invention are prepared to perform the present methods, the common descriptions between them are omitted in order to avoid undue redundancy leading to the complexity of this specification.

According to an embodiment of the present invention, the primers for detecting the mpb64 gene may comprise a hybridizing nucleotide sequence to an mpb64 gene sequence.

According to an embodiment of the present invention, the primers for detecting the RD9 gene may comprise a hybridizing nucleotide sequence to an RD9 gene sequence.

According to an embodiment of the present invention, the primers for detecting the RD1 gene deletion may comprise: (i) a hybridizing nucleotide sequence to an upstream portion from the 5'-end of a deletion site of the RD1 gene; (ii) a hybridizing nucleotide sequence to a downstream portion from the 3'-end of the deletion site of the RD1 gene; or (iii) a hybridizing nucleotide sequence to a junction portion formed by deletion of the RD1 gene.

According to an embodiment of the present invention, the primers for detecting the RD4 gene deletion may comprise: (i) a hybridizing nucleotide sequence to an upstream portion from the 5'-end of a deletion site of the RD4 gene; (ii) a hybridizing nucleotide sequence to a downstream portion from the 3'-end of the deletion site of the RD4 gene; or (iii) a hybridizing nucleotide sequence to a junction portion formed by deletion of the RD4 gene.

According to an embodiment of the present invention, a sequence of the upstream portion from the 5'-end of the deletion site of the RD1 gene may comprise a sequence selected from the group consisting of the sequence of SEQ ID NO: 1, the sequence of SEQ ID NO: 2, and sequences having a homology of 80% or higher thereto; and a sequence of the downstream portion from the 3'-end of the deletion site of the RD1 gene may comprise a sequence selected from the group consisting of the sequence of SEQ ID NO: 3, the sequence of SEQ ID NO: 4, and sequences having a homology of 80% or higher thereto.

According to an embodiment of the present invention, a sequence of the upstream portion from the 5'-end of the deletion site of the RD4 gene may comprise a sequence selected from the group consisting of the sequence of SEQ ID NO: 5, the sequence of SEQ ID NO: 6, and sequences having a homology of 80% or higher thereto; and a sequence of the downstream portion from the 3'-end of the deletion site of the RD4 gene may comprise a sequence selected from the group consisting of SEQ ID NO: 7, SEQ ID NO: 8, and sequences having a homology of 80% or higher thereto.

According to an embodiment of the present invention, nucleic acid amplification composition may further comprises (i) a probe for detecting the mpb64 gene, (ii) a probe for detecting the RD9 gene, (iii) a probe for detecting the RD1 gene deletion, or (iv) a probe for detecting the RD4 gene deletion.

According to an embodiment of the present invention, *M. bovis* BCG may be *M. bovis* BCG with the mpb64 gene deletion.

In a specific embodiment of the present invention, the *M. bovis* BCG with the mpb64 gene deletion includes *M. bovis* BCG Pasteur, *M. bovis* BCG phipps, *M. bovis* BCG Copenhagen, *M. bovis* BCG Glaxo, and *M. bovis* BCG Tice, but is not limited thereto.

According to an embodiment of the present invention, the nucleic acid amplification composition may further comprise a pair of primers for detecting a gene for screening *M. tuberculosis, M. bovis,* and *M. bovis* BCG, and the screening gene may include a genes present in all of *M. tuberculosis, M. bovis,* and *M. bovis* BCG, for example, mpb70 and IS6110, but is not limited thereto.

In an embodiment of the present invention, the gene for screening *M. tuberculosis; M. bovis,* and *M. bovis* BCG may be mpb70.

All of the present nucleic acid amplification composition described hereinabove may optionally include the reagents required for performing target amplification reactions (e.g., PCR reactions) such as buffers, DNA polymerase cofactors, and deoxyribonucleotide-5-triphosphates. Optionally, the nucleic acid amplification composition may also include various polynucleotide molecules, reverse transcriptase, various buffers and reagents, and antibodies that inhibit DNA polymerase activity. The nucleic acid amplification composition may also include reagents necessary for performing positive and negative control reactions. Optimal amounts of reagents to be used in a given reaction can be readily determined by the skilled artisan having the benefit of the current disclosure. The components of the nucleic acid amplification composition may be present in separate containers, or multiple components may be present in a single container.

The features and advantages of this invention will be summarized as follows:

The present invention can detect a single infection of *M. tuberculosis, M. bovis,* and *M. bovis* BCG and a co-infection with two pathogens by combining the results on the presence or absence of the mpb64 gene, the presence or absence of the RD9 gene, the presence or absence of the RD1 gene deletion and the presence or absence of the RD4 gene deletion.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example: Detection of *M. tuberculosis, M. bovis,* and *M. bovis* BCG Pathogens

The present inventors confirmed that the method of the present invention can determine the presence or absence of *M. tuberculosis, M. bovis,* and *M. bovis* BCG pathogens individually and in combination of two thereof.

Example 1: Preparation of Target Nucleic Acid and Oligonucleotide

In order to determine the presence or absence of *M. tuberculosis, M. bovis,* and *M. bovis* BCG pathogens, the presence or absence of an mpb64 gene, the presence or absence of an RD9 gene, the presence or absence of an RD1 gene deletion, and the presence or absence of an RD4 gene deletion were identified. The TaqMan real-time PCR method (U.S. Pat. Nos. 5,210,015 and 5,538,848) was employed to determine the presence or absence of the genes or the presence or absence of the gene deletion.

Taq DNA polymerase having a 5' nuclease activity was used for the extension of forward primers and reverse primers, the cleavage of TaqMan probe. Genomic DNA of *M. tuberculosis,* genomic DNA of *M. bovis,* and genomic DNA of *M. bovis* BCG were used as target nucleic acid.

A 4× oligonucleotide mix comprising a pair of primers for detecting an mpb64 gene (SEQ ID NO: 21 and SEQ ID NO: 22), a pair of primers for detecting an RD9 gene(SEQ ID NO: 24 and SEQ ID NO: 25), a pair of primers for detecting an RD1 gene deletion(SEQ ID NO: 27 and SEQ ID NO: 28), and a pair of primers for detecting an RD4 gene deletion (SEQ ID NO: 30 and SEQ ID NO: 31), each in a concentration of 0.25 µM, and a probe for detecting an mpb64 gene(SEQ ID NO: 23), a probe for detecting an RD9 gene(SEQ ID NO: 26), a probe for detecting an RD1 gene deletion (SEQ ID NO: 29), and a probe for detecting an RD4 gene deletion (SEQ ID NO: 32), each in a concentration of 0.1 µM was prepared.

The probe was labeled with a fluorescent reporter molecule at its 5'-end and a quencher molecule at its 3'-end. The Probe was blocked with a carbon spacer at their 3'-ends to prohibit their extension.

In Table 3, oligonucleotide sequences used in the Example are listed.

TABLE 3

| Target | Oligo type | SEQ ID NO. | Sequence |
|---|---|---|---|
| mpb64 | Forward primer | 21 | 5'-GCACCCAACGACCAC GTA-3' |
|  | Reverse primer | 22 | 5'-CTTCGGGCAGCAACT CCC-3' |
|  | TaqMan probe | 23 | 5'-[CAL Fluor Red 610]GCGCTATCGATACC TGTTGTCCGGT[BHQ-2]-3' |
| RD9 | Forward primer | 24 | 5'-GAAAATTACTACCGG AGCAGC-3' |
|  | Reverse primer | 25 | 5'-GTCAGCATGGCCAGA TGG-3' |
|  | TaqMan probe | 26 | 5'-[Quasar 670]GCT TAGTGACGACGCGCTGGC G[BHQ-2]-3' |
| RD1del | Forward primer | 27 | 5'-CCTGAAGAAGCGGTT GCC-3' |
|  | Reverse primer | 28 | 5'-AAGCGAGGTGACCAC CCG-3' |
|  | Junction portion probe | 29 | 5'-[FAM]CGACGATTGG CACATCCAGCCG[BHQ-1]-3' |
| RD4del | Forward primer | 30 | 5'-TGTGAACGCGACGAC CTC-3' |
|  | Reverse primer | 31 | 5'-GTAGCGTTACTGAGA AATTGCTG-3' |
|  | Junction portion probe | 32 | 5'-[CAL Fluor Orange 560]CCATTGGTAATTTT TGGGAGCGGC[BHQ-1]-3' |

Example 2: Real-Time PCR and Target Signal Detection

The real-time PCR was performed using the target nucleic acid and the 4× oligonucleotide mix, prepared in Example 1.

Six tubes containing *M. tuberculosis* (tube 1), *M. bovis* (tube 2), M. bovis BCG (tuve 3), *M. bovis*, and *M. bovis* BCG (tube 4), *M. bovis* and *M. tuberculosis* (tube 5), and *M. bovis* BCG and *M. tuberculosis* (tube 6), respectively, and a negative control tube (tube 7) containing no target nucleic acids were prepared as follows:

The real-time PCR was conducted in the final volume of 20 μl containing a target nucleic acid (100 pg of *M. tuberculosis* genomic DNA, 100 pg of *M. bovis* genomic DNA, 100 pg of *M. bovis* BCG genomic DNA, a mixture of 100 pg of *M. bovis* genomic DNA and 100 pg of *M. bovis* BCG genomic DNA, a mixture of 100 pg of *M. bovis* genomic DNA and 100 pg of *M. tuberculosis* genomic DNA, or a mixture of 100 pg of *M. bovis* BCG genomic DNA and 100 pg of *M. tuberculosis* genomic DNA), 5 μl of the 4× oligonucleotide mix, and 5 μl of a 4× master mix [final, 200 μM dNTPs, 2 mM $MgCl_2$, and 2U Taq DNA polymerase]. The tubes containing the reaction mixture were placed in the real-time thermocycler (CFX96, Bio-Rad) and then the reaction mixtures were subjected to denaturation at 95° C. for 15 min followed by 50 cycles of 30 sec at 95° C., 60 sec at 60° C., and 30 sec at 72° C. The detection of signals was performed at 60° C. every cycle. Ct values were calculated using auto calculated single thresholds.

Figure 3:
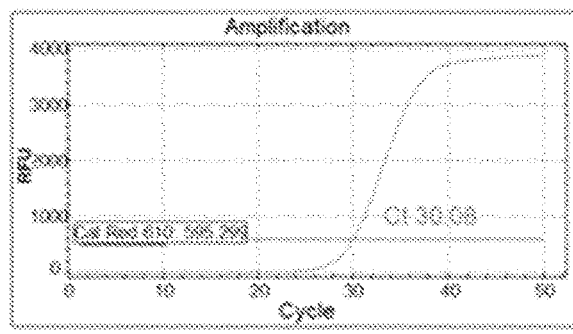
FIG. 3 shows experiment results for tube 1 where *M. tuberculosis* alone exists.
Figure 3:
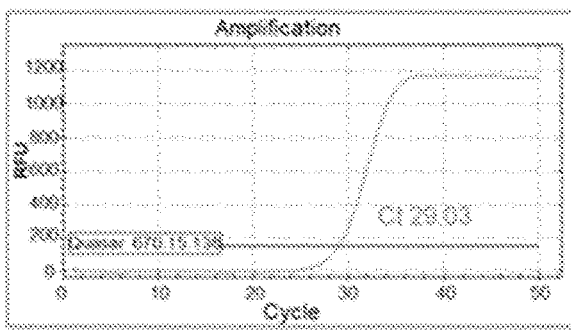
Figure 3:
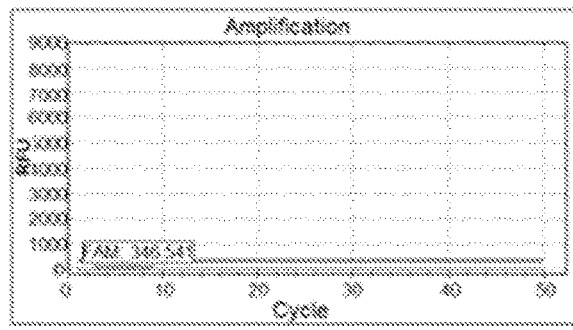
Figure 3:
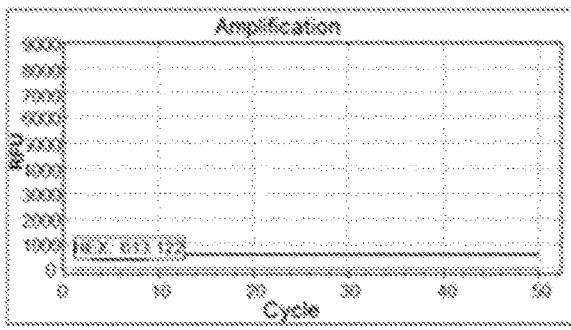

In tube 1 where the *M. tuberculosis* was present alone, as shown in FIG. 3, no signals were detected for RD1 gene deletion and RD4 gene deletion whereas a signal (Ct 30.08) for the mpb64 gene and a signal (Ct 29.03) for the RD9 gene were detected. This data implicates the absence of the RD1 gene deletion, the absence of the RD4 gene deletion, and the presence of the RD9 gene, coinciding with the determination criterion for the presence of *M. tuberculosis* pathogen alone as shown in Table 2.

Figure 4:
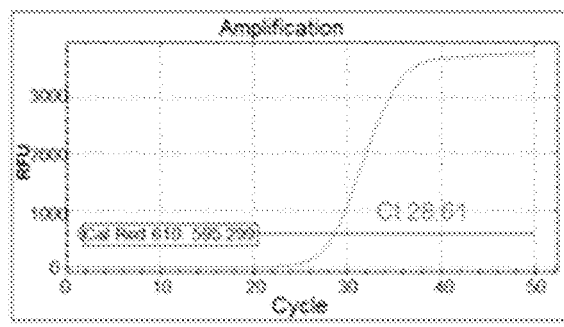
FIG. 4 shows experiment results for tube 2 where *M. bovis* alone exists.
Figure 4:
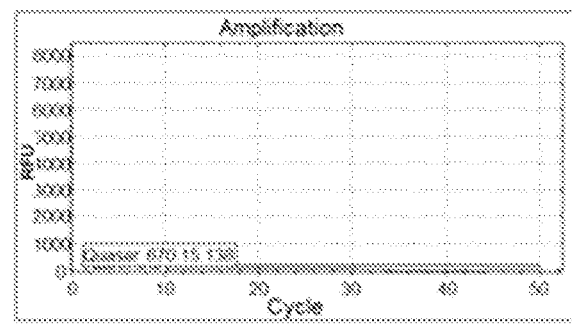
Figure 4:
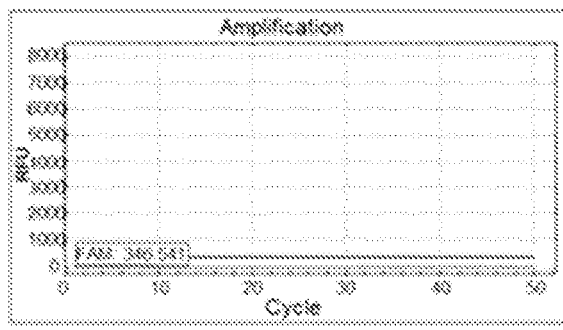
Figure 4:
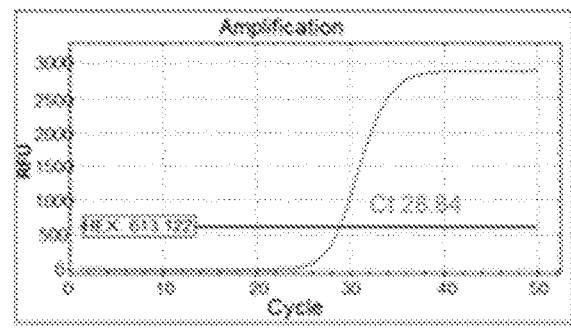

In tube 2 where the *M. bovis* was present alone, as shown in FIG. 4, no signals were detected for the RD9 gene and the RD1 gene deletion whereas only a signal (Ct 28.61) for the mpb64 gene and a signal (Ct 28.84) for the RD4 gene deletion were detected. This data implicates the presence of the mpb64 gene, the presence of the RD1 gene deletion, the presence of the RD4 gene deletion, and the absence of the RD9 gene, coinciding with the determination criterion for the presence of *M. bovis* pathogen alone as shown in Table 2.

Figure 5:
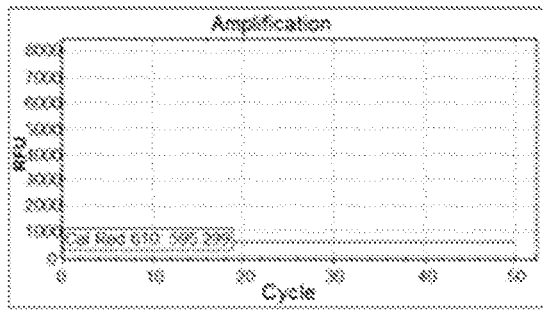
FIG. 5 shows experiment results for tube 3 where *M. bovis* BCG alone exists.
Figure 5:
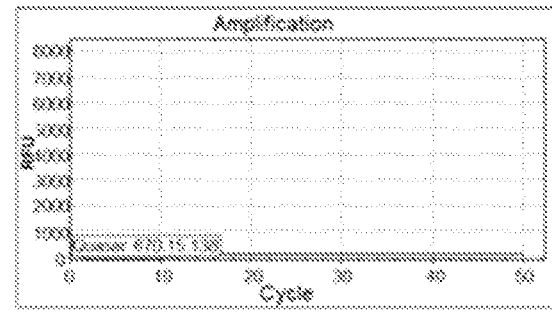
Figure 5:
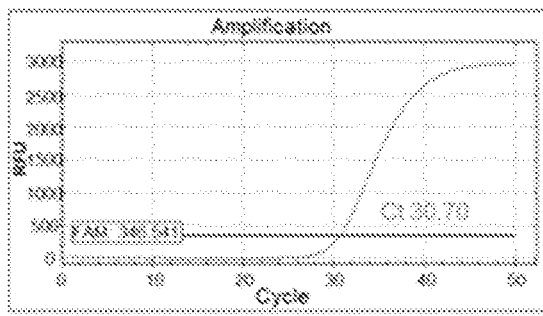
Figure 5:
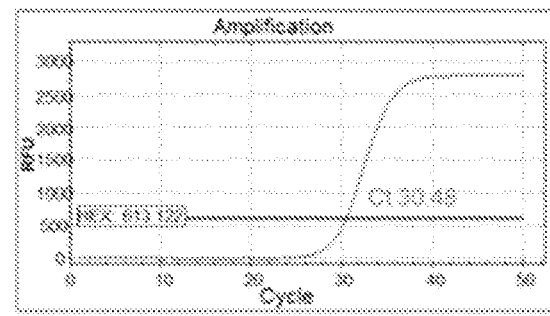

In tube 3 where the *M. bovis* BCG present alone, as shown in FIG. 5, no signals were detected for the presence of the mpb64 gene and the RD9 gene, a signal (Ct 30.70) for RD1 gene deletion and a signal for (Ct 30.48) for RD4 gene deletion. This data implicates the absence of the mpb64 gene, the present of the RD1 gene deletion, and the absence of the RD9 gene, coinciding with the determination criterion for the presence of *M. bovis* BCG pathogen alone as shown in Table 2.

Figure 6:
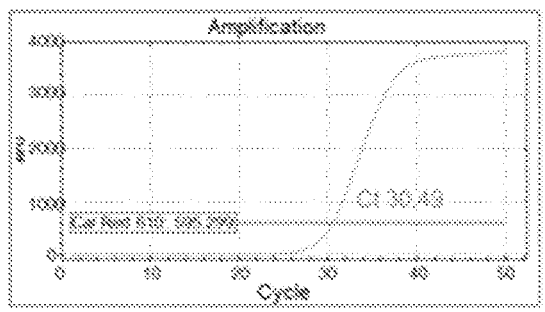
FIG. 6 shows experiment results for tube 4 where *M. tuberculosis* and *M. bovis* coexist.
Figure 6:
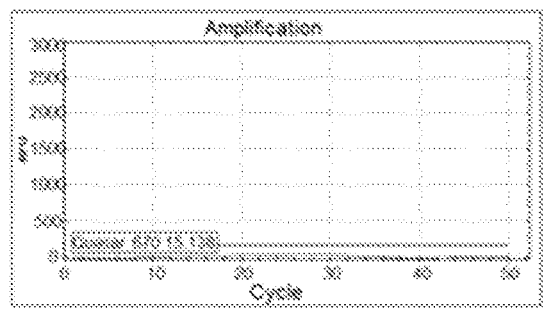
Figure 6:
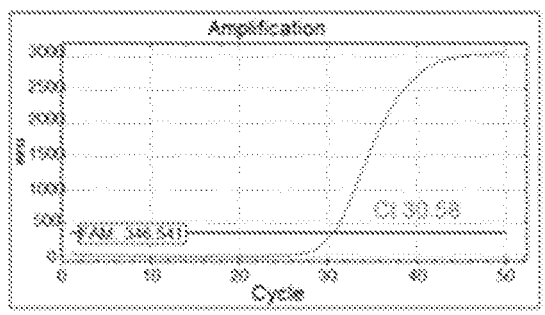
Figure 6:
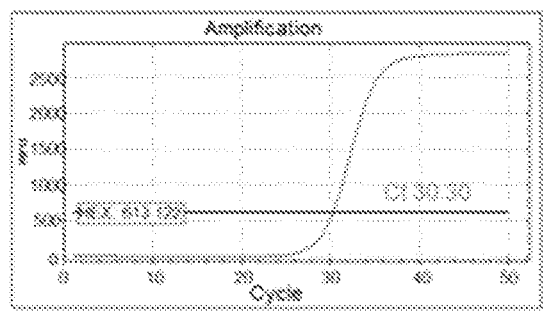

In tube 4 wherein *M. bovis* and *M. bovis* BCG coexisted, as shown in FIG. 6, no signals for the RD9 gene were detected whereas a signal (Ct 30.49) for the mpb64 gene, a signal (Ct 30.58) for the RD1 gene deletion, and a signal (Ct 30.30) for the RD4 gene deletion were detected. This data implicates the presence of the mpb64 gene, the presence of the RD1 gene deletion, the presence of the RD4 gene deletion, and the absence of the RD9 gene, coinciding with the determination criterion for the co-existence of the two pathogens *M. bovis*, and *M. bovis* BCG as shown in Table 2.

Figure 7:
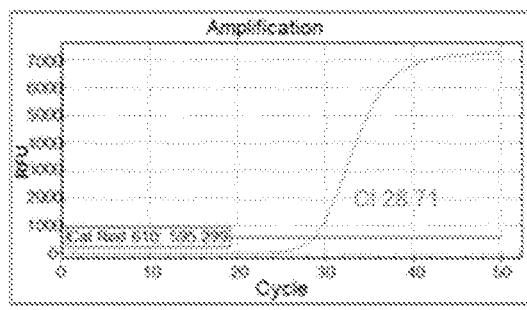
FIG. 7 shows experiment results for tube 5 where *M. tuberculosis* and *M. bovis* BCG coexist.
Figure 7:
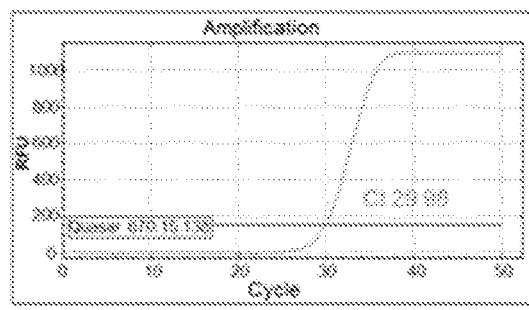
Figure 7:
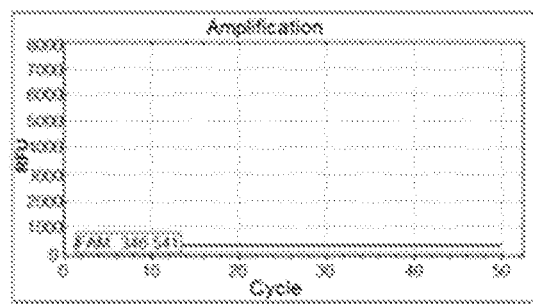
Figure 7:
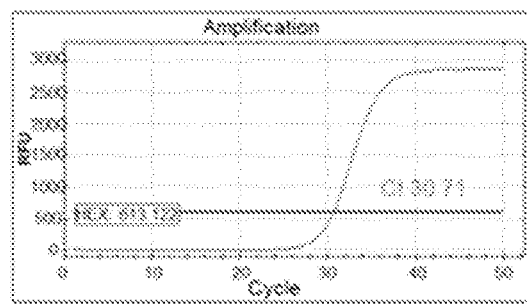

In tube 5 wherein *M. bovis* and *M. tuberculosis* coexisted, as shown in FIG. 7, no signals were detected for the RD1 gene deletion whereas a signal (Ct 28.71) for the mpb64 gene, a signal (Ct 29.98) for the RD9 gene, and a signal (Ct 30.71) for the RD4 gene deletion were detected. This data implicates the presence of the mpb64 gene, the absence of the RD1 gene deletion, the presence of the RD4 gene deletion, and the presence of the RD9 gene, coinciding with the determination criterion for the co-existence of the two pathogens M. bovis and M. tuberculosis, as shown in Table 2.

Figure 8:
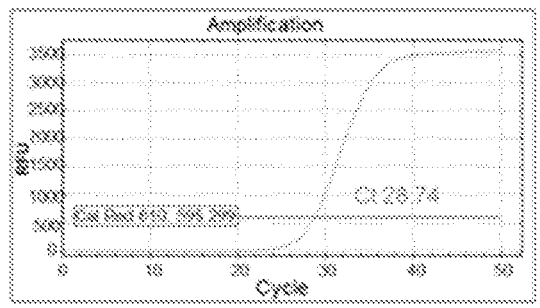
FIG. 8 shows experiment results for tube 6 where *M. bovis* and *M. bovis* BCG coexist.
Figure 8:
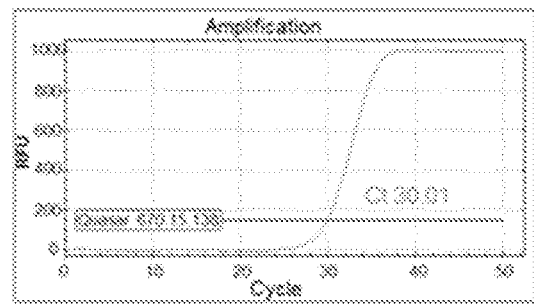
Figure 8:
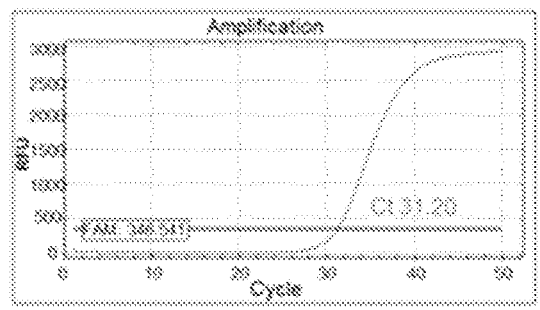
Figure 8:
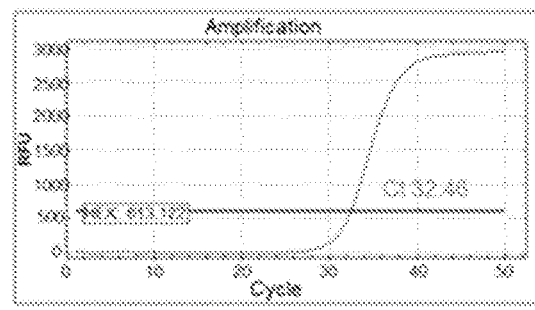

In tube 6 where *M. bovis* BCG and *M. tuberculosis* coexisted, as shown in FIG. 8, a signal (Ct 28.74) for the mpb64 gene, a signal (Ct 30.01) for the RD9 gene, a signal (Ct 31.20) for the RD1 gene deletion, and a signal (Ct 32.46) for the RD4 gene deletion were detected. This data implicates the presence of the RD1 gene deletion and the presence of the RD9 gene, coinciding with the determination criterion for the coexistence of the two pathogens *M. bovis* BCG and *M. tuberculosis* as shown in Table 2.

Figure 9:
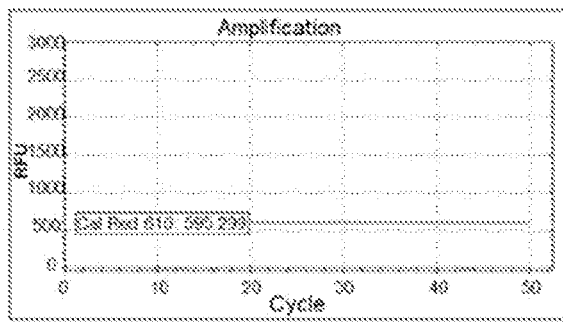
FIG. 9 shows experiment results for control (negative) tube 7 where no target nucleic acids are present.
Figure 9:
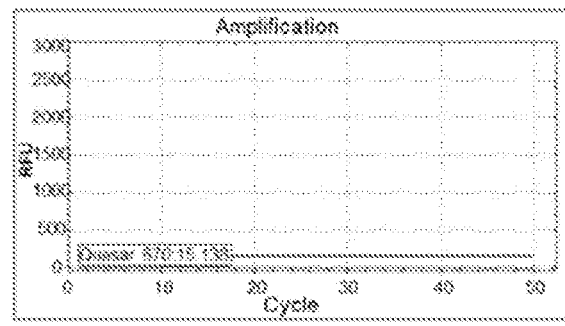
Figure 9:
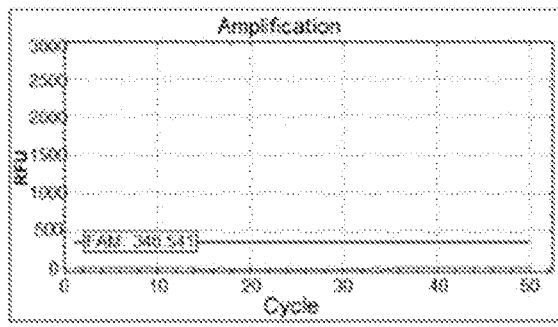
Figure 9:
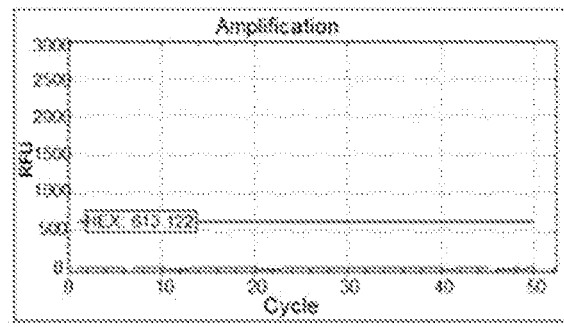

In contrast, no signals were detected from the control tube 7 where no target nucleic acids existed, as shown in FIG. 9.

Therefore, the detection method of the present invention was identified to be able to determine the presence of *M. tuberculosis, M. bovis*, and *M. bovis* BCG individually and the coexistence of two of *M. tuberculosis, M. bovis*, and *M. bovis* BCG.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. A method for determining the presence or absence of *Mycobacterium tuberculosis, Mycobacterium bovis*, and *Mycobacterium bovis* BCG in a sample comprising nucleic acid molecules, the method comprising:
   (a) mixing a sample comprising nucleic acid molecules with a nucleic acid amplification composition comprising (i) a pair of primers for detecting an mpb64 gene; (ii) a pair of primers for detecting an RD9 gene; (iii) a pair of primers for detecting an RD1 gene deletion; and (iv) a pair of primers for detecting an RD4 gene deletion, wherein the pair of primers for detecting the mpb64 gene or the RD9 gene produce an amplicon when the mpb64 gene or the RD9 gene is present, and the pair of primers for detecting the RD1 gene deletion or the RD4 gene deletion produce an amplicon when the RD1 gene deletion or the RD4 gene deletion is present;
   (b) performing a nucleic acid amplification reaction;
   (c) determining the presence or absence of the mpb64 gene, the presence or absence of the RD9 gene, the presence or absence of the RD1 gene deletion, and the presence or absence of the RD4 gene deletion, from results of the nucleic acid amplification reaction; and
   (d) determining the presence or absence of *M. tuberculosis, M. bovis*, and *M. bovis* BCG, respectively by using results obtained in step (c).

2. The method of claim 1, wherein the *M. bovis* BCG is *M. bovis* BCG with a deletion of the mpb64 gene.

3. The method of claim 1, wherein in step (d),
   (i) *M. tuberculosis* is determined to be present in the sample if the presence of the RD9 gene is determined;
   (ii) *M. bovis* is determined to be present in the sample if the presence of the mpb64 gene, the absence of the RD1 gene deletion, and the presence of the RD4 gene deletion are determined; or
   (iii) *M. bovis* BCG is determined to be present in the sample if the absence of the mpb64 gene and the presence of the RD1 gene deletion are determined.

4. The method of claim 3, wherein in step (d),
   (i) *M. tuberculosis* is determined to be present alone in the sample if the absence of the RD1 gene deletion, the absence of the RD4 gene deletion, and the presence of the RD9 gene are determined;
   (ii) *M. bovis* is determined to be present alone in the sample if the presence of the mpb64 gene, the absence of the RD1 gene deletion, the presence of the RD4 gene deletion, and the absence of the RD9 gene are determined;
   (iii) *M. bovis* BCG is determined to be present alone in the sample if the absence of the mpb64 gene, the presence of the RD1 gene deletion, and the absence of the RD9 gene are determined;
   (iv) *M. bovis* and *M. bovis* BCG are determined to be simultaneously present in the sample if the presence of the mpb64 gene, the presence of the RD1 gene deletion, the presence of the RD4 gene deletion, and the absence of the RD9 gene are determined;
   (v) *M. bovis* and *M. tuberculosis* are determined to be simultaneously present in the sample if the presence of the mpb64 gene, the absence of the RD1 gene deletion, the presence of the RD4 gene deletion, and the presence of the RD9 gene are determined; or
   (vi) *M. bovis* BCG and *M. tuberculosis* are determined to be simultaneously present in the sample if the presence of the RD1 gene deletion and the presence of the RD9 gene are determined.

5. The method of claim 1, wherein
   (i) the primers for detecting the mpb64 gene comprise a hybridizing nucleotide sequence to an mpb64 gene sequence;
   (ii) the primers for detecting the RD9 gene comprise a hybridizing nucleotide sequence to an RD9 gene sequence;
   (iii) the primers for detecting the RD1 gene deletion comprise: (iii-1) a hybridizing nucleotide sequence to an upstream portion from the 5'-end of a deletion site of the RD1 gene; (iii-2) a hybridizing nucleotide sequence to a downstream portion from the 3'-end of the deletion site of the RD1 gene; or (iii-3) a hybridizing nucleotide sequence to a junction portion formed by deletion of the RD1 gene; or
   (iv) the primers for detecting the RD4 gene deletion comprise: (iv-1) a hybridizing nucleotide sequence to an upstream portion from the 5'-end of a deletion site of the RD4 gene; (iv-2) a hybridizing nucleotide sequence to a downstream portion from the 3'-end of the deletion site of the RD4 gene; or (iv-3) a hybridizing nucleotide sequence to a junction portion formed by deletion of the RD4 gene.

6. The method of claim 5, wherein
   (i) a sequence of the upstream portion from the 5'-end of the deletion site of the RD1 gene comprises a sequence selected from the group consisting of SEQ ID NO: 1, SEQ ID NO: 2, and sequences having 80% or higher homology thereto; and a sequence of the downstream portion from the 3'-end of the deletion site of the RD1 gene comprises a sequence selected from the group consisting of SEQ ID NO: 3, SEQ ID NO: 4, and sequences having 80% or higher homology thereto; or
   (ii) a sequence of the upstream portion from the 5'-end of the deletion site of the RD4 gene comprises a sequence selected from the group consisting of SEQ ID NO: 5, SEQ ID NO: 6, and sequences having 80% or higher homology thereto; and a sequence of the downstream portion from the 3'-end of the deletion site of the RD4 gene comprises a sequence selected from the group consisting of SEQ ID NO: 7, SEQ ID NO: 8, and sequences having 80% or higher homology thereto.

7. The method of claim 1, wherein the amplicon is detected by post-PCR detection or real-time detection.

8. The method of claim 1, wherein the nucleic acid amplification composition further comprises (i) a probe for detecting the mpb64 gene, (ii) a probe for detecting the RD9 gene, (iii) a probe for detecting the RD1 gene deletion, or (iv) a probe for detecting the RD4 gene deletion.

9. The method of claim 8, wherein (i) when the primers and probe for detecting the RD1 gene deletion comprise hybridizing nucleotide sequences to the upstream portion from the 5'-end of the deletion site of the RD1 gene or the downstream portion from the 3'-end of the deletion site of the RD1 gene, the probe and one primer of the pair of primers, which has the same orientation as the probe, comprise hybridizing nucleotide sequences to different portions from each other; or (ii) when the primers and probe for detecting the RD4 gene deletion comprise hybridizing nucleotide sequences to the upstream portion from the 5'-end of the deletion site of the RD4 gene or the downstream portion from the 3'-end of the deletion site of the RD4 gene, the probe and one primer of the pair of primers, which has the same orientation as the probe, comprise hybridizing nucleotide sequences to different portions from each other.

10. The method of claim 1, wherein the nucleic acid amplification composition further comprises a pair of primers for detecting an mpb70 gene.

* * * * *

SEQUENCE LISTING

```
<160> NUMBER OF SEQ ID NOS: 36

<210> SEQ ID NO 1
<211> LENGTH: 296
<212> TYPE: DNA
<213> ORGANISM: Mycobacterium sp.

<400> SEQUENCE: 1
gggcaagacg accattgccc acgcgatcgc gcgcgccatt tgtgcccgaa acagtcccca        60
gcaggtgcgg ttcatgctcg cggactaccg ctcgggcctg ctggacgcgg tgccggacac       120
ccatctgctg ggcgccggcg cgatcaaccg caacagcgcg tcgctagacg aggccgttca       180
agcactggcg gtcaacctga agaagcggtt gccgccgacc gacctgacga cggcgcagct       240
acgctcgcgt tcgtggtgga gcggatttga cgtcgtgctt ctggtcgacg attggc          296

<210> SEQ ID NO 2
<211> LENGTH: 306
<212> TYPE: DNA
<213> ORGANISM: Mycobacterium sp.

<400> SEQUENCE: 2
cggttacgct ggttaattat gacgtccgtt accaccgagc gccccgtgcg acagcgcggc        60
cagcgcaagc gaggtgacca cccggctgat cgcccaagcg gtgcatcatg cgcgcggatt       120
caacgggtta ctgcgaatac cggcgcgggg tggatccagc ggccgagccg gcgtgaaatg       180
ccggaggcca accggacggt gatccgcgag gcgatctggc ggtttgggga gggcagtagg       240
ggatgagtat taccaggccg acgggcagct atgccagaca gatgctggat ccgggcggct       300
ggatgt                                                                 306

<210> SEQ ID NO 3
<211> LENGTH: 306
<212> TYPE: DNA
<213> ORGANISM: Mycobacterium sp.

<400> SEQUENCE: 3
acatccagcc gcccggatcc agcatctgtc tggcatagct gcccgtcggc ctggtaatac        60
tcatccccta ctgccctccc caaaccgcca gatcgcctcg cggatcaccg tccggttggc       120
ctccggcatt tcacgccggc tcggccgctg gatccacccc gcgccggtat tgcagtaac        180 ccgttgaatc cgcgcgcatg atgcaccgct tgggcgatca gccgggtggt cacctcgctt       240
gcgctggccg cgctgtcgca cggggcgctc ggtggtaacg gacgtcataa ttaaccagcg       300
taaccg                                                                 306

<210> SEQ ID NO 4
<211> LENGTH: 296
<212> TYPE: DNA
<213> ORGANISM: Mycobacterium sp.
```

<400> SEQUENCE: 4

| | | | | | |
|---|---|---|---|---|---|
| gccaatcgtc | gaccagaagc | acgacgtcaa | atccgctcca | ccacgaacgc | gagcgtagct | 60 |
| gcgccgtcgt | caggtcggtc | ggcggcaacc | gcttcttcag | gttgaccgcc | agtgcttgaa | 120 |
| cggcctcgtc | tagcgacgcg | ctgttgcggt | tgatcgcgcc | ggcgcccagc | agatgggtgt | 180 |
| ccggcaccgc | gtccagcagg | cccgagcggt | agtccgcgag | catgaaccgc | acctgctggg | 240 |
| gactgtttcg | ggcacaaatg | gcgcgcgcga | tcgcgtgggc | aatggtcgtc | ttgccc | 296 |

<210> SEQ ID NO 5
<211> LENGTH: 300
<212> TYPE: DNA
<213> ORGANISM: Mycobacterium sp.

<400> SEQUENCE: 5

| | | | | | |
|---|---|---|---|---|---|
| ccgttcagtt | tggcgtaggc | cagcgccacg | aacatcgcgt | gggactccgg | cggaaagcgt | 60 |
| tgtgcgacct | cgtcgaaggc | cactaaaggc | aggccgcaaa | actcggacac | gcttgcatag | 120 |
| tctcggtcga | ctgtgaacgc | gacgacctca | tattccgaat | cccttgtgaa | gtagtaatgt | 180 |
| gcgagctgag | cgatgtcgcc | gctcccaaaa | attaccaatg | gtttggtcat | gacgccttcc | 240 |
| taaccagaat | tgtgaattca | tacaagccgt | agtcgtgcag | aagcgcaaca | ctcttggagt | 300 |

<210> SEQ ID NO 6
<211> LENGTH: 300
<212> TYPE: DNA
<213> ORGANISM: Mycobacterium sp.

<400> SEQUENCE: 6

| | | | | | |
|---|---|---|---|---|---|
| catcgcgcat | gaacaccagc | acggctagcg | cgatgccgac | accgccacc | atgccgccca | 60 |
| cccagaaggc | gaacagattc | agcatgggcc | gacgccgcga | cagcatgacg | accgcgagtc | 120 |
| ccagacgcgc | cgggtcaatc | gccatcccca | accccaaaag | gagcaccatc | gtccacatca | 180 |
| gtggggacgc | tactacggca | cggcgcgccc | cgtagcgtta | ctgagaaatt | gctgaaaaat | 240 |
| ggctattgac | cagctaagat | atccggtacg | cccgcgccgc | ggagagcgcc | gttgtaggcc | 300 |

<210> SEQ ID NO 7
<211> LENGTH: 300
<212> TYPE: DNA
<213> ORGANISM: Mycobacterium sp.

<400> SEQUENCE: 7

| | | | | | |
|---|---|---|---|---|---|
| ggcctacaac | ggcgctctcc | gcggcgcggg | cgtaccggat | atcttagctg | gtcaatagcc | 60 |
| attttcagc | aatttctcag | taacgctacg | gggcgcgccg | tgccgtagta | gcgtccccac | 120 |
| tgatgtggac | gatggtgctc | cttttggggt | tggggatggc | gattgacccg | gcgcgtctgg | 180 |
| gactcgcggt | cgtcatgctg | tcgcggcgtc | ggcccatgct | gaatctgttc | gccttctggg | 240 |
| tgggcggcat | ggtggcgggt | gtcggcatcg | cgctagccgt | gctggtgttc | atgcgcgatg | 300 |

<210> SEQ ID NO 8
<211> LENGTH: 300
<212> TYPE: DNA
<213> ORGANISM: Mycobacterium sp.

<400> SEQUENCE: 8

| | | | | | |
|---|---|---|---|---|---|
| actccaagag | tgttgcgctt | ctgcacgact | acggcttgta | tgaattcaca | attctggtta | 60 |
| ggaaggcgtc | atgaccaaac | cattggtaat | ttttgggagc | ggcgacatcg | ctcagctcgc | 120 |

```
acattactac ttcacaaggg attcggaata tgaggtcgtc gcgttcacag tcgaccgaga    180
ctatgcaagc gtgtccgagt tttgcggcct gcctttagtg gccttcgacg aggtcgcaca    240
acgctttccg ccggagtccc acgcgatgtt cgtggcgctg gcctacgcca aactgaacgg    300
```

```
<210> SEQ ID NO 9
<211> LENGTH: 58
<212> TYPE: DNA
<213> ORGANISM: Mycobacterium sp.

<400> SEQUENCE: 9
ggtcccaatc gaaggccttg tacgtggtcg ttgggtgcgt gccgccggcg ttctggta     58

<210> SEQ ID NO 10
<211> LENGTH: 60
<212> TYPE: DNA
<213> ORGANISM: Mycobacterium sp.

<400> SEQUENCE: 10
gattttcttc ttcaacccgg gggagttgct gcccgaagca gccggcccaa cccaggtatt    60

<210> SEQ ID NO 11
<211> LENGTH: 61
<212> TYPE: DNA
<213> ORGANISM: Mycobacterium sp.

<400> SEQUENCE: 11
cagccgtgga cgacacgggc gctgctccgg tagtaatttt cggcggccgc agccagatcg    60
g                                                                    61

<210> SEQ ID NO 12
<211> LENGTH: 58
<212> TYPE: DNA
<213> ORGANISM: Mycobacterium sp.

<400> SEQUENCE: 12
ctggcgtttc tttccgaacg ccatctggcc atgctgacca cgctgcgggc ggacaact      58

<210> SEQ ID NO 13
<211> LENGTH: 58
<212> TYPE: DNA
<213> ORGANISM: Mycobacterium sp.

<400> SEQUENCE: 13
ccgtcgtcag gtcggtcggc ggcaaccgct tcttcaggtt gaccgccagt gcttgaac      58

<210> SEQ ID NO 14
<211> LENGTH: 58
<212> TYPE: DNA
<213> ORGANISM: Mycobacterium sp.

<400> SEQUENCE: 14
gcaccgcttg ggcgatcagc cgggtggtca cctcgcttgc gctggccgcg ctgtcgca      58

<210> SEQ ID NO 15
<211> LENGTH: 58
<212> TYPE: DNA
<213> ORGANISM: Mycobacterium sp.

<400> SEQUENCE: 15
tcacaaggga ttcggaatat gaggtcgtcg cgttcacagt cgaccgagac tatgcaag      58
```

```
<210> SEQ ID NO 16
<211> LENGTH: 63
<212> TYPE: DNA
<213> ORGANISM: Mycobacterium sp.

<400> SEQUENCE: 16
gctggtcaat agccattttt cagcaatttc tcagtaacgc tacggggcgc gccgtgccgt    60
agt                                                                 63

<210> SEQ ID NO 17
<211> LENGTH: 65
<212> TYPE: DNA
<213> ORGANISM: Mycobacterium sp.

<400> SEQUENCE: 17
aaggtgaact gagcaagcag accggacaac aggtatcgat agcgccgaat gccggcttgg    60
acccg                                                               65

<210> SEQ ID NO 18
<211> LENGTH: 62
<212> TYPE: DNA
<213> ORGANISM: Mycobacterium sp.

<400> SEQUENCE: 18
agatggcgtt cggaaagaaa cgccagcgcg tcgtcactaa gccgcgtagt ggtgttgacc    60
at                                                                  62

<210> SEQ ID NO 19
<211> LENGTH: 62
<212> TYPE: DNA
<213> ORGANISM: Mycobacterium sp.

<400> SEQUENCE: 19
agacagatgc tggatccggg cggctggatg tgccaatcgt cgaccagaag cacgacgtca    60
aa                                                                  62

<210> SEQ ID NO 20
<211> LENGTH: 64
<212> TYPE: DNA
<213> ORGANISM: Mycobacterium sp.

<400> SEQUENCE: 20
tgtgcgagct gagcgatgtc gccgctccca aaaattacca atggtttggt catgacgcct    60
tcct                                                                64

<210> SEQ ID NO 21
<211> LENGTH: 18
<212> TYPE: DNA
<213> ORGANISM: Artificial Sequence
<220> FEATURE:
<223> OTHER INFORMATION: MPB64 F Primer

<400> SEQUENCE: 21
gcacccaacg accacgta                                                 18

<210> SEQ ID NO 22
<211> LENGTH: 18
<212> TYPE: DNA
<213> ORGANISM: Artificial Sequence
<220> FEATURE:
<223> OTHER INFORMATION: MPB64 R Primer
```

```
<400> SEQUENCE: 22
cttcgggcag caactccc                                                    18

<210> SEQ ID NO 23
<211> LENGTH: 25
<212> TYPE: DNA
<213> ORGANISM: Artificial Sequence
<220> FEATURE:
<223> OTHER INFORMATION: MPB64 Probe

<400> SEQUENCE: 23
gcgctatcga tacctgttgt ccggt                                            25

<210> SEQ ID NO 24
<211> LENGTH: 21
<212> TYPE: DNA
<213> ORGANISM: Artificial Sequence
<220> FEATURE:
<223> OTHER INFORMATION: RD9 F Primer

<400> SEQUENCE: 24
gaaaattact accggagcag c                                                21

<210> SEQ ID NO 25
<211> LENGTH: 18
<212> TYPE: DNA
<213> ORGANISM: Artificial Sequence
<220> FEATURE:
<223> OTHER INFORMATION: RD9 R Primer

<400> SEQUENCE: 25
gtcagcatgg ccagatgg                                                    18

<210> SEQ ID NO 26
<211> LENGTH: 22
<212> TYPE: DNA
<213> ORGANISM: Artificial Sequence
<220> FEATURE:
<223> OTHER INFORMATION: RD9 Probe

<400> SEQUENCE: 26
gcttagtgac gacgcgctgg cg                                               22

<210> SEQ ID NO 27
<211> LENGTH: 18
<212> TYPE: DNA
<213> ORGANISM: Artificial Sequence
<220> FEATURE:
<223> OTHER INFORMATION: RD1del F Primer

<400> SEQUENCE: 27
cctgaagaag cggttgcc                                                    18

<210> SEQ ID NO 28
<211> LENGTH: 18
<212> TYPE: DNA
<213> ORGANISM: Artificial Sequence
<220> FEATURE:
<223> OTHER INFORMATION: RD1del R Primer

<400> SEQUENCE: 28
aagcgaggtg accacccg                                                    18

<210> SEQ ID NO 29
<211> LENGTH: 22
```

```
<212> TYPE: DNA
<213> ORGANISM: Artificial Sequence
<220> FEATURE:
<223> OTHER INFORMATION: RD1del Probe

<400> SEQUENCE: 29
cgacgattgg cacatccagc cg                                          22

<210> SEQ ID NO 30
<211> LENGTH: 18
<212> TYPE: DNA
<213> ORGANISM: Artificial Sequence
<220> FEATURE:
<223> OTHER INFORMATION: RD4del F Primer

<400> SEQUENCE: 30
tgtgaacgcg acgacctc                                               18

<210> SEQ ID NO 31
<211> LENGTH: 23
<212> TYPE: DNA
<213> ORGANISM: Artificial Sequence
<220> FEATURE:
<223> OTHER INFORMATION: RD4del R Primer

<400> SEQUENCE: 31
gtagcgttac tgagaaattg ctg                                         23

<210> SEQ ID NO 32
<211> LENGTH: 24
<212> TYPE: DNA
<213> ORGANISM: Artificial Sequence
<220> FEATURE:
<223> OTHER INFORMATION: RD4del Probe

<400> SEQUENCE: 32
ccattggtaa tttttgggag cggc                                        24

<210> SEQ ID NO 33
<211> LENGTH: 702
<212> TYPE: DNA
<213> ORGANISM: Mycobacterium sp.

<400> SEQUENCE: 33
acaacatcaa catcagcctg cccagttact accccgacca gaagtcgctg gaaaattaca    60
tcgcccagac gcgcgacaag ttcctcagcg cggccacatc gtccactcca cgcgaagccc   120
cctacgaatt gaatatcacc tcggccacat accagtccgc gataccgccg cgtggtacgc   180
aggccgtggt gctcaaggtc taccagaacg ccggcggcac gcacccaacg accacgtaca   240
aggccttcga ttgggaccag gcctatcgca agccaatcac ctatgacacg ctgtggcagg   300
ctgacaccga tccgctgcca gtcgtcttcc ccattgtgca aggtgaactg agcaagcaga   360
ccggacaaca ggtatcgata gcgccgaatg ccggcttgga cccggtgaat tatcagaact   420
tcgcagtcac gaacgacggg gtgattttct tcttcaaccc gggggagttg ctgcccgaag   480
cagccggccc aacccaggta ttggtccac gttccgcgat cgactcgatg ctggcctaga   540
ctcgcgagga ccgcgcggtg gtcactgcgc ggatttgggg cggcggaagt gagtgttcgg   600
tgcgcccact gcggtgactc acctgcagcg ccggcatcga caggccggga gctcaagaat   660
cgtcgctaga gaatctatgg tgcgttagag gattccctgc ta                     702

<210> SEQ ID NO 34
```

```
<211> LENGTH: 702
<212> TYPE: DNA
<213> ORGANISM: Mycobacterium sp.

<400> SEQUENCE: 34
tagcagggaa tcctctaacg caccatagat tctctagcga cgattcttga gctcccggcc    60
tgtcgatgcc ggcgctgcag gtgagtcacc gcagtgggcg caccgaacac tcacttccgc   120
cgccccaaat ccgcgcagtg accaccgcgc ggtcctcgcg agtctaggcc agcatcgagt   180
cgatcgcgga acgtgggacc aatacctggg ttgggccggc tgcttcgggc agcaactccc   240
ccgggttgaa gaagaaaatc accccgtcgt tcgtgactgc gaagttctga taattcaccg   300
ggtccaagcc ggcattcggc gctatcgata cctgttgtcc ggtctgcttg ctcagttcac   360
cttgcacaat ggggaagacg actggcagcg gatcggtgtc agcctgccac agcgtgtcat   420
aggtgattgg cttgcgatag gcctggtccc aatcgaaggc cttgtacgtg tcgttgggt    480
gcgtgccgcc ggcgttctgg tagaccttga gcaccacggc ctgcgtacca cgcggcggta   540
tcgcggactg gtatgtggcc gaggtgatat tcaattcgta gggggcttcg cgtggagtgg   600
acgatgtggc cgcgctgagg aacttgtcgc gcgtctgggc gatgtaattt ccagcgact   660
tctggtcggg gtagtaactg ggcaggctga tgttgatgtt gt                     702

<210> SEQ ID NO 35
<211> LENGTH: 585
<212> TYPE: DNA
<213> ORGANISM: Mycobacterium sp.

<400> SEQUENCE: 35
ggcgtcgcgc acggcgtcga tgtcgctgtt caccgccgcc ctaccctcca gtgagagcca    60
gcgcgcgccg tcgacctggc tgagcacggc aagcccactg cggtcggcat tgacggcctt   120
ttgggagccg ccggtggtga tgacccgcgc gatgtgagtc ttggggtcga aggtgaaacc   180
taccgccacc acgtgcggcg agttgtccgc ccgcagcgtg gtcagcatgg ccagatggcg   240
ttcggaaaga aacgccagcg cgtcgtcact aagccgcgta gtggtgttga ccatcgccac   300
tcacgctagc gcaggcaata atcgcagccg tggacgacac gggcgctgct ccggtagtaa   360
ttttcggcgg ccgcagccag atcggcggcg aactcgcgcg acgcctggct gccggggcga   420
cgatggtgct ggccgcgcgg aacgccgatc aactcgccga ccaggccgcc gcactccgcg   480
cagctggcgc tatagcggtg cacacccggg agttcgacgc cgacgacctg gccgcacacg   540
gcccgttggt cgcttcgctc gttgccgagc acggccccat cggca                  585

<210> SEQ ID NO 36
<211> LENGTH: 585
<212> TYPE: DNA
<213> ORGANISM: Mycobacterium sp.

<400> SEQUENCE: 36
tgccgatggg gccgtgctcg gcaacgagcg aagcgaccaa cgggccgtgt gcggccaggt    60
cgtcggcgtc gaactcccgg gtgtgcaccg ctatagcgcc agctgcgcgg agtgcggcgg   120
cctggtcggc gagttgatcg gcgttccgcg cggccagcac catcgtcgcc ccggcagcca   180
ggcgtcgcgc gagttcgccg ccgatctggc tgcggccgcc gaaaattact accggagcag   240
cgcccgtgtc gtccacggct gcgattattg cctgcgctag cgtgagtggc gatggtcaac   300
accactacgc ggcttagtga cgacgcgctg gcgtttcttt ccgaacgcca tctgccatg   360
ctgaccacgc tgcgggcgga caactcgccg cacgtggtgg cggtaggttt caccttcgac   420
```

```
cccaagactc acatcgcgcg ggtcatcacc accggcggct cccaaaaggc cgtcaatgcc    480
gaccgcagtg ggcttgccgt gctcagccag gtcgacggcg cgcgctggct ctcactggag    540
ggtagggcgg cggtgaacag cgacatcgac gccgtgcgcg acgcc                    585
```